(12) United States Patent
Hearing, Jr.

(10) Patent No.: US 6,579,848 B1
(45) Date of Patent: Jun. 17, 2003

(54) DEPIGMENTING ACTIVITY OF AGOUTI SIGNAL PROTEIN AND PEPTIDES THEREOF

(75) Inventor: Vincent J. Hearing, Jr., Clarksburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/983,157

(22) PCT Filed: Jun. 21, 1996

(86) PCT No.: PCT/US96/10695

§ 371 (c)(1),
(2), (4) Date: Dec. 22, 1997

(87) PCT Pub. No.: WO97/00892

PCT Pub. Date: Jan. 9, 1997

Related U.S. Application Data

(60) Provisional application No. 60/000,436, filed on Jun. 23, 1995.

(51) Int. Cl.[7] .................. A61K 38/16; C07K 14/47; C07K 16/18; G01N 33/68
(52) U.S. Cl. .................. 514/12; 514/13; 514/14; 514/15; 514/16; 514/21; 514/44; 530/300; 530/324; 530/326; 530/328; 530/350
(58) Field of Search .................. 514/12, 2, 13, 514/14, 15, 16, 17, 18, 21, 44; 530/300, 324, 325, 326, 327, 328, 329, 330, 350; 435/6, 91.2; 536/23.1, 23.3, 24.33; 424/401

(56) References Cited

U.S. PATENT DOCUMENTS

| | | | | |
|---|---|---|---|---|
| 5,126,327 A | * | 6/1992 | Takeuchi et al. | 514/18 |
| 5,510,332 A | * | 4/1996 | Kogan et al. | 514/14 |
| 5,650,489 A | * | 7/1997 | Lam et al. | 530/334 |
| 5,789,651 A | * | 8/1998 | Woychik | 435/69.1 |
| 6,296,857 B1 | * | 10/2001 | Schonrock et al. | 424/401 |

FOREIGN PATENT DOCUMENTS

| | | | |
|---|---|---|---|
| WO | 94/04568 | * | 3/1994 |
| WO | 95/00115 | * | 1/1995 |

OTHER PUBLICATIONS

Kohmura et al. Inhibition of Angiotensin–Converting Enzyme by Synthetic Peptide Fragments of Human Kappa–Casein. Agric. Biol. Chem. 1990, vol. 54, No. 3, pp. 835–836.*

Wilson et al., "Structure and Function of ASP, The Human Homolog of the Mouse Agouti Gene, Human Molecular Genetics", vol. 4, No. 2, pp 223–230, 1995.*

(List continued on next page.)

*Primary Examiner*—Jeffrey E. Russel
(74) *Attorney, Agent, or Firm*—Needle & Rosenberg, P.C.

(57) ABSTRACT

The invention is an agouti signaling protein and peptides as well as pharmaceutical compositions thereof and their use in methods of inhibiting melanin production by melanocytes. The agouti signaling protein and peptides thereof are useful in cosmetics and in clinical prevention and treatment of hyperpigmentary conditions. Methods for screening peptides for melanogenesis inhibiting activity are also provided.

19 Claims, 14 Drawing Sheets

OTHER PUBLICATIONS

Kwon et al., "Molecular Structure and Chromosomal Mapping of the Human Homolog of the Agouti Gene", Proc. Natl. Acad. Sci. USA, vol. 91, pp 9760–9764, Oct. 1994.*

Wilson et al. "Structure and Function of ASP, the Human Homolog of the Mouse Agouti Gene" *Human Molecular Genetics*, 4(2):223–230, Abstract No. 95276734, Feb. 1995.

Kwon et al. "Molecular Structure and Chromosomal Mapping of the Human Homolog of the Agouti Gene" *Proc. Natl. Acad.Sci. USA* 91:9760–9764, Oct. 1994.

Miller et al. "Cloning of the Mouse Agouti Gene Predicts a Secreted Protein Ubiquitously Expressed in Mice carrying the Lethal Yellow Mutation", *Genes & Development* 7(3):454–467, Abstract No. 93194064, Mar. 1993.

Tripathi et al. "Mutational Mapping of the Catalytic Activities of Human Tyrosinase" *J. Biologic. Chem.* 267 (33):23707–23712, Nov. 25, 1992.

Jackson et al. "A Second Tyrosinase–Related Protein, TRP–2 Maps to and is Mutated at the Mouse Slaty Locus" *EMBO J.* 1(2):527–535, 1992.

Thody, Anthony J. and Burchill, Susan A. "Tyrosinase and the Regulation of Coat Color Changes in $C_3H$–HeA$^{vy}$ Mice" *Pigment Cell Res.* 5:335–339, 1992.

Kappenman et al. Tyrosinase Abundance and Activity in Murine Hairbulb Melanocytes of Agouti Mutants (C57BL/6J–a/a, Ay/a, and AwJ/AwJ) *Pigment Cell Res. Suppl.* 2:79–83, 1992.

Tsukamoto et al. "A Second Tyrosinase–Related Protein, TRP–2, is a Melanogenic Enzyme Termed DOPAchrome Tautomerase" *EMBO J.* 11(2):519–526, 1992.

Sakai et al. "Modulation of Murine Melanocyte Function in vitro by Agouti Signal Protein" *EMBO J.* 16(12):3544–3552, 1997.

Furumura et al. "The Interaction of Agouti Signal Protein and Melanocyte Stimulating Hormone to Regulate Melanin Formation in Mammals" *Pigment Cell Res.* 9:191–203, 1996.

Kobayashi et al. "Modulation of Melanogenic Protein Expression During the Switch from eu–to Pheomelanogenesis" *J. Cell Science* 108:2301–2309, 1995.

Rosemblat et al. "Identification of a Melanosomal Membrane Protein Encoded by the Pink–eyed Dilution (Type II Oculocutaneous Albinism) Gene" *Proc. Natl. Acad. Sci. USA* 91 :12071–12075, Dec. 1994.

Lu et al. "Agouti Protein is an Antagonist of the Melanocyte–Stimulating–Hormone Receptor" *Nature* 371:799–802, Oct. 27, 1994.

Jiménez–Cervantes et al. "A New Enzymatic Function in the Melanogenic Pathway" *J. of Biol. Chem.* 269(27):17993–18001, Jul. 8, 1994.

Zhou et al. "Identification of a Melanosomal Matrix Protein Encoded by the Murine si (silver) Locus using 'Organelle Scanning'" *Proc. Natl. Acad. Sci. USA* 91:7076–7080, Jul. 1994.

Kobayashi et al. "Tyrosinase Related Protein 1 (TRP1) Functions as a DHICA Oxidase in Melanin Biosynthesis" *EMBO J.* 13(24):5818–5825, 1994.

del Marmol et al. "TRP–1 Expression Correlates with Eumelanogenesis in Human Pigment Cells in Culture" *FEBS* 327(3):307–310, Aug. 1993.

Chiu et al. "Postnatal Ocular Expression of Tyrosinase and Related Proteins: Disruption by the Pink–eyed Unstable ($P^{un}$) Mutation" *Exp. Eye. Res.* 57:301–305, 1993.

Miller et al. "Cloning of the Mouse Agouti Gene Predicts a Secreted Protein Ubiquitously Expressed in Mice Carrying the Lethal Yellow Mutation" *Genes & Development* 7:454–467, 1993.

Hearing, Vincent J. and King, Richard A., "Determinants of Skin Color: Melanocytes and Melanization", Chapter 1, Part 1—Basic Science Aspects of Pigmentation, by CRC Press, Inc., pp 3–31, 1993.

Ito, Shosuke "Biochemistry and Physiology of Melanin", Chapter 1, Part 2—Basic Aspects of Pigmentation, by CRC Press, Inc., pp 33–59, 1993.

Bultman et al. "Molecular Characterization of the Mouse Agouti Locus" *Cell* 71 :1195–1204, Dec. 24, 1992.

* cited by examiner

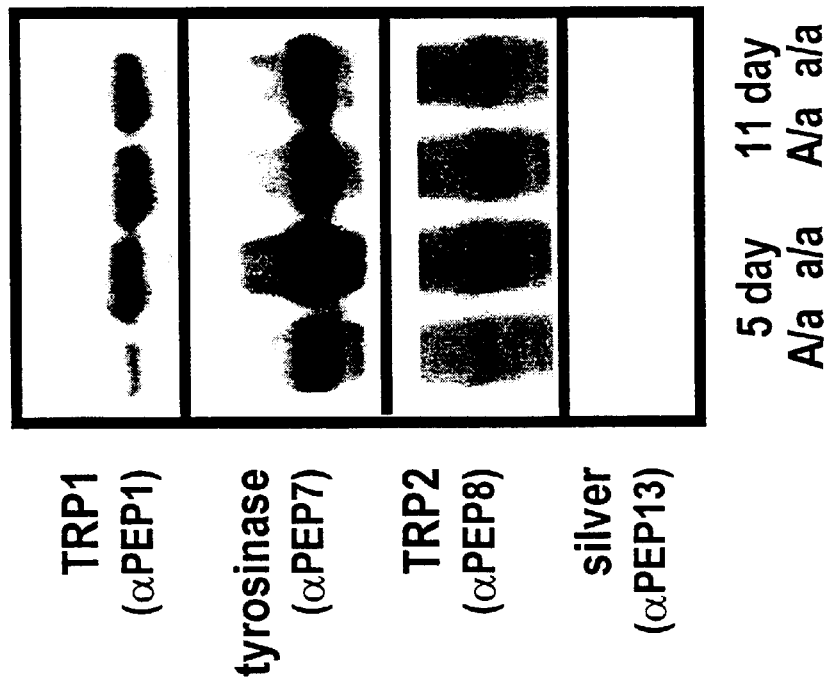

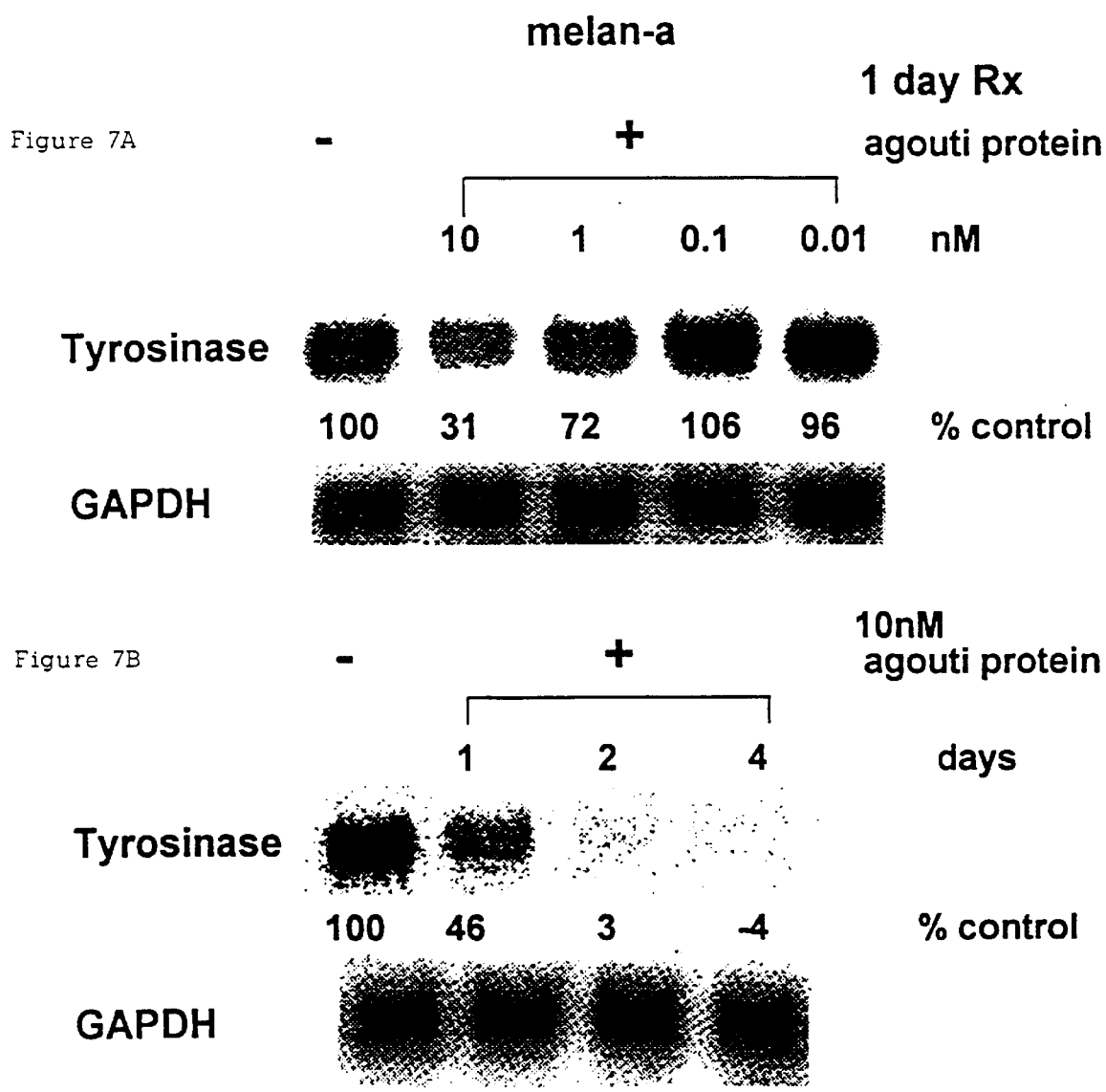

Ultrastructural study
melan-a
− +
5 days Rx
agouti protein (10nM)
(x8000)
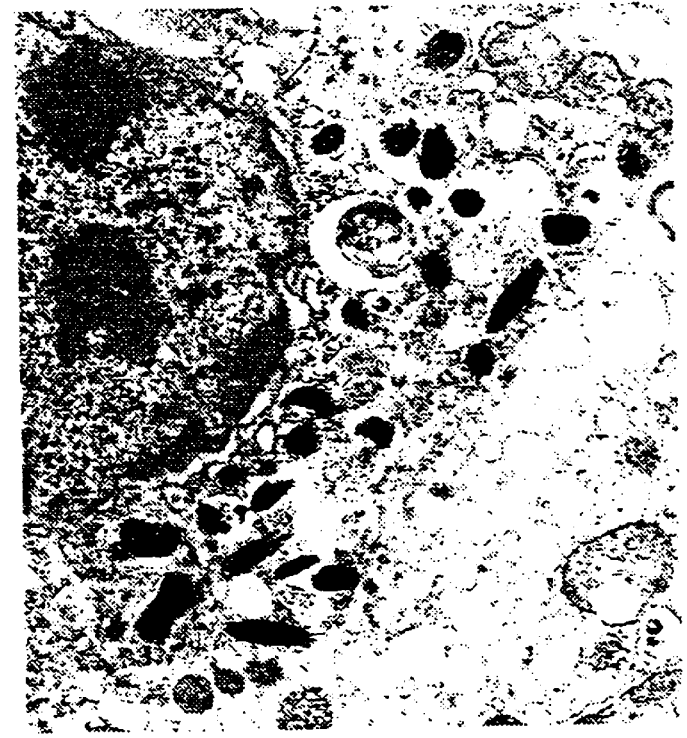
Figure 8A
Figure 8B Figure 13
Northern blotting
|  | B16F10 | | | | 5 days Rx |
|---|---|---|---|---|---|
|  | − | + | − | + | MSH (10nM) |
|  | − | − | + | + | agouti protein (10nM) |
Tyrosinase 
100    217    134    210    %control
TRP1 
100    157    62    182    %control
TRP2 
100    163    77    173    %control
MSH-R 
100    125    195    144    %control
GAPDH 

DEPIGMENTING ACTIVITY OF AGOUTI SIGNAL PROTEIN AND PEPTIDES THEREOF

The present application is a 35 U.S.C. 371 application of PCT/US96/10695 filed Jun. 21, 1996, which claims the benefit of U.S. provisional application No. 60/000,436 filed Jun. 23, 1995.

BACKGROUND OF THE INVENTION

Mammalian melanocytes can produce two types of melanin, eumelanin (which is black and/or brown in color) and pheomelanin (which is red and/or yellow in color) (Prota, 1992; Ito, 1993a). Switching between these two types of melanins in follicular (i.e. hair bulb) melanocytes elicits a temporary shift from eu- to pheomelanogenesis, which is responsible for the wild-type agouti pigment pattern of murine hair color, i.e. a yellow striped band against a black background on each hair shaft, as reviewed by Silvers (1979) and Hirobe (1991). This physiological switch is controlled by the agouti locus, which has recently been cloned (Bultman et al., 1992; Miller et al., 1993). The agouti locus-encoded protein is thought to be secreted by nonmelanocytic follicular cells (Silvers, 1958) and functions as an antagonist of the melanocyte-stimulating hormone (αMSH) receptor, which is expressed specifically by melanocytes (Lu et al., 1994). The recessive black mutation (nonagouti; a) at the agouti locus results in a nearly complete loss of agouti RNA which causes the constitutive production of eumelanin black hairs. In contrast, the dominant lethal yellow mutation (Ay/a) elicits the ubiquitous ectopic production of agouti RNA in nearly all tissues of the body and throughout the entire phase of the hair growth cycle, prompting the production of completely yellow pheomelanic hairs (Ito and Fujita, 1985; Duhl et al., 1994a,b).

For many decades, melanosomal proteins that regulate melanin biosynthesis have been studied and characterized, especially those required for eumelanogenesis, as reviewed by Hearing and Tsukamoto (1991) and Hearing and King (1993). Tyrosine (EC 1.14.18.1), which is encoded at the albino locus, is the essential enzymatic protein for both types of melanin formation. Tyrosinase is a trifunctional enzyme with three catalytic activities: tyrosine to 3,4-dihydroxyphenyl-alanine (DOPA), the oxidation of DOPA to dopaquinone and the oxidation of 5,6-dihydroxlindole (DHI) to indole-5,6-quinone (Korner and Pawelek, 1982; Hearing, 1987; Tripathi et al., 1992). Other tyrosine-related proteins (TRP) have been shown to regulate eumelanogenesis catalytically at steps distal to tyrosinase. TRP1, encoded at the brown locus, functions as 5,6-dihydroxyindole-2-carboxylic acid (DHICA) oxidase (Jimenez-Cervantes et al., 1994; Kobayashi et al., 1994b) while TRP2, encoded at the slaty locus, functions as DOPAchrome tautomerase (EC5.3.2.3) (Barber et al., 1984; Aroca et al., 1990; Tsukamoto et al., 1992; Jackson et al., 1992). The silver locus-encoded protein had been proposed to function in melanogenesis catalytically within the melanosome, and although it has some limited homology to the tyrosinase-related proteins (Kwon et al., 1991), it has been recently demonstrated to be a melanosomal matrix protein and to have none of the known melanogenic activities (Zhou et al., 1994; Kobayashi et al., 1994a). The product of the pink-eyed dilution locus is also a melanosomal protein that actively participates in the regulation of melanogenesis (Tamate et al., 1989; Chiu et al., 1993; Rosemblat et al., 1994).

During pheomelanogenesis, the activity and expression of tyrosinase has been reported to be lower than that found during eumelanogenesis (Barber et al., 1985; Burchill et al, 1986, 1989; Lamoreux et al, 1986; Movaghar and Hunt, 1987; Tamate et al., 1989; Granholm et al., 1990; Kappenman et al., 1992). In addition to tyrosinase, thiols are essential to capture the dopaquinone made enzymatically by tyrosinase in order to produce the cysteinyldopas necessary for pheomelanogenesis (FIG. 1). Subsequent cyclization and polymerization of cysteinyldopas in an uncharacterized series of reactions results in the production of the high molecular mass complex known as pheomelanin (Prota, 1992; Hearing and King, 1993; Ito, 1993 a). The switch between eu- and pheomelanogenesis has been proposed to be regulated enzymatically primarily at the level of tyrosinase (Ito, 1993a). The potential roles of other melanogenic gene products during pheomelanogenesis, however, remain unclear, since there have been few studies about the expression and function of such proteins during pheomelanogenesis. To date, only the absence of DOPAchrome tautomerase activity in yellow mice has been reported (Barber et al., 1985), as has the absence of TRP1 mRNA expression in pheomelanogenic mice (Thody and Burchill, 1992) and human melanoma cells (Del-Marmol et al, 1993).

The present invention determines the transcriptional and translational levels of the expression and catalytic functions of tyrosinase, TRP1, TRP2 and the silver protein during pheomelanogenesis. The expression and melanogenic activities of those proteins in hair bulbs of wild type agouti mice during their pheomelanogenic phase is also determined in the present invention. The present invention shows that TRP1, TRP2 and the silver protein function specifically in eumelanogenesis and may play an important role in the production of eumelanosomes. The down-regulation of expression of those proteins during melanogenesis is shown in the present invention using agouti signaling protein.

SUMMARY OF THE INVENTION

The present invention is a biologically active peptide of the Agouti Signaling Protein which has depigmenting activity.

The present invention is a method of down-regulating one or more melanogenic enzymes involved in melanin synthesis.

The present invention is also the use of the Agouti signaling protein and biologically active peptides thereof in methods of inhibiting melanin synthesis.

A further aspect of the invention is the treatment of hyperpigmentary conditions and diseases using an effective amount of agouti signaling protein or peptides thereof.

Another aspect of the invention is a pharmaceutical composition of agouti signaling protein or biologically active peptides thereof and a pharmaceutically acceptable carrier.

The present invention is also a method for screening for biologically active peptides of the agouti signaling protein and other compounds useful in inhibiting melanin synthesis.

BRIEF DESCRIPTION OF THE FIGURES

These and other objects, features, and many of the attendant advantages of the invention will be better understood upon a reading of the following detailed description when considered in connection with the accompanying drawings wherein:

FIGS. 6A and 6B show expression of melanogenic proteins of dorsal skins of agouti (A/a) and black (a/a) mice. Expression of melanogenic proteins in dorsal skins of 5 and 11 day newborn sibling agouti and black mice was examined using western immunoblotting, and metabolic labeling and immunoprecipitation, as detailed in Materials and Methods. (FIG. 6A) Proteins in extracts of dorsal skins of agouti and black mice were solubilized and analyzed by western immunoblotting, as detailed for FIG. 2; 40 μg protein of each dorsal skin extract (10 μg of the melan-a cell extract) was separated in each lane. (FIG. 6B) Skin tissues in organ culture was labeled with [$^{35}$S]methionine for 6 hours, solubilized and analyzed by immunoprecipitation, as detailed in Materials and Methods.

FIGS. 7A and 7B show the Northern blot analysis of RNA levels of tyrosinase and GAPDH from melan-a cells cultured in the presence of various concentrations of agouti protein (FIG. 7A) and cultured in the presence of 10 nM of agouti protein for 1, 2 or 4 days (FIG. 7B).

FIGS. 8A and 8B show the ultrastructure of melan-a cells grown for five days in the presence of 10 nM agouti protein (FIG. 8B) or in the absence of agouti protein (FIG. 8A) (mag ×8000).

FIG. 13 shows the Northern blot analysis of RNA levels of tyrosinase, TRP 1, TRP 2, MSH-R and GAPDH from melan-a cells cultured 5 days in the presence or absence of 10 nM MSH, in the presence or absence of 10 nM agouti protein, or in the presence of both MSH and agouti protein.

DETAILED DESCRIPTION OF THE INVENTION

Figure 1:
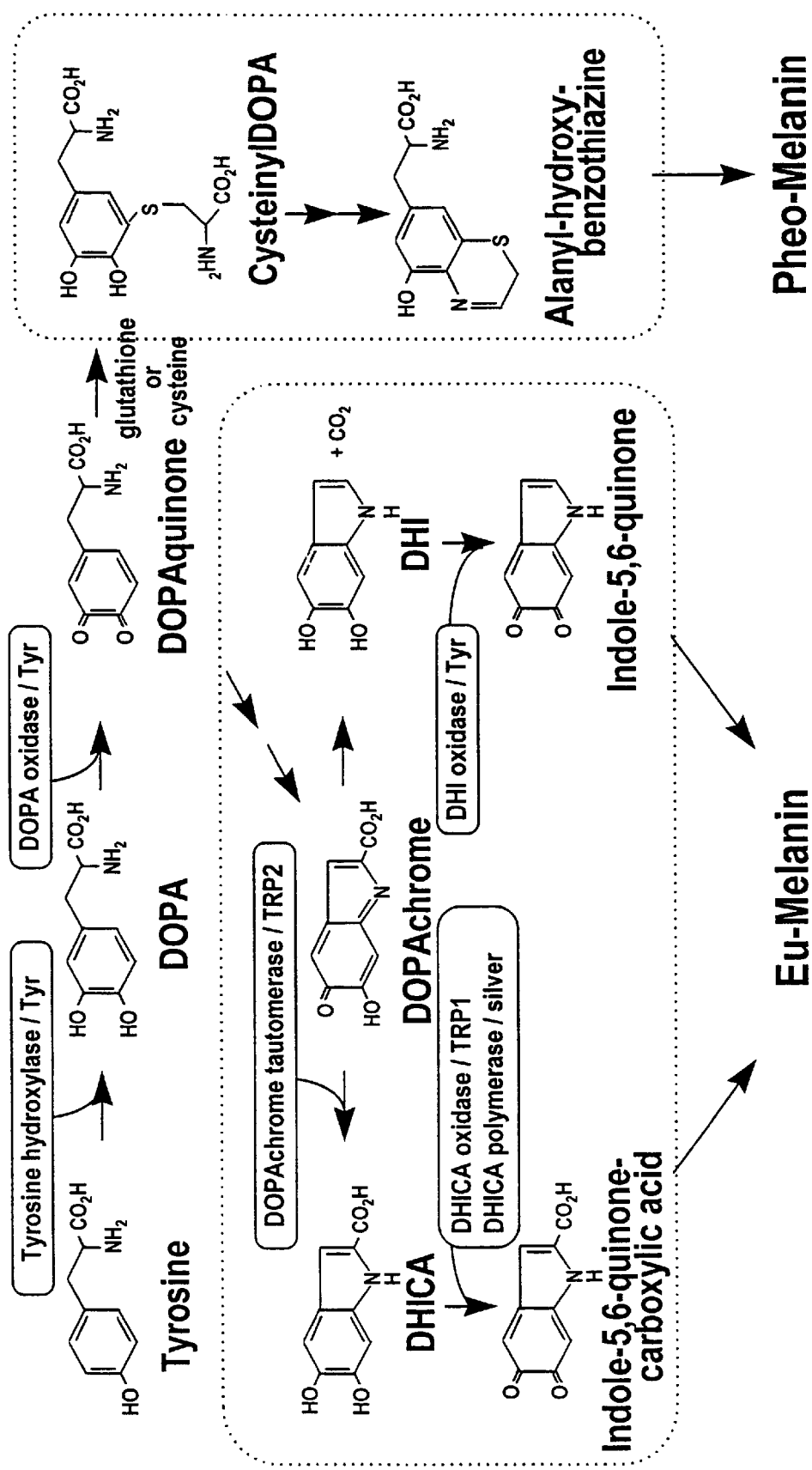
FIG. 1 shows the eumelanin and pheomelanin biosynthetic pathway.

The present invention is a physiological extrinsic inhibitor of melanogenesis in mammals. An inhibitor of melanogenesis of the present invention is a protein and peptides thereof that inhibit the production of melanin. A preferred inhibitor of melanogenesis of the present invention is agouti signaling protein and biologically active peptides thereof. Thus, the invention is a method of treating a hyperpigmentary condition in a subject, comprising administering to the subject the agouti signaling protein or a biologically active peptide thereof The agouti signaling protein and peptides thereof are useful for cosmetic purposes and for clinical application in the prevention or treatment of various hyperpigmentary conditions and diseases. Such conditions or diseases include but are not limited to melasma photoaging spots, solar keratosis, and post-inflammatory hyperpigmentation such as occurs at sites of wound healing.

Polypeptide and peptide are terms used interchangeably herein to designate a linear series of amino acid residues connected one to the other by peptide bonds between the alpha-amino and carboxy groups of adjacent residues. The polypeptide and peptide may be a synthetic peptide or polypeptide, recombinant peptide or recombinant polypeptide or a peptide or polypeptide derived from enzymatic cleavage of the naturally occurring full length protein.

Synthetic peptide refers to a chemically produced chain of amino acid residues linked together by peptide bonds that is free of naturally occurring proteins and fragments thereof.

As used herein, the phrase "agouti signaling peptide" refers to a polypeptide or peptide having an amino acid residue sequence that comprises an amino acid residue sequence that corresponds, and preferably is identical, to a portion of the murine agouti signaling protein or the human homolog. The amino acid residue sequence of the mature murine agouti signaling protein is disclosed in Miller et al Gene & Development 7:454–467, 1993 and is listed as SEQ ID NO: 1. The amino acid sequence of the mature human homolog to the agouti signaling protein is disclosed in Wilson, B. D. et al Human Mol. Genetics. 4(2):223–230, 1995 and is listed as SEQ ID No: 2. A peptide of the present invention has the capacity to inhibit the production of melanin.

```
Agouti Signal Protein (131 residues for murine)
(mouse) H2N-MET-ASP-VAL-THR-ARG-LEU-LEU-LEU-ALA-THR-LEU-VAL-SER-PHE-
(human)     MET-ASP-VAL-THR-ARG-LEU-LEU-LEU-ALA-THR-LEU-LEU-GLY-PHE-
            signal sequence →                            *    *

LEU-CYS-PHE-PHE-THR-VAL-HIS-SER-HIS-LEU-ALA-LEU-GLU-GLU-
            LEU-CYS-PHE-PHE-THR-ALA-ASN-SER-HIS-LEU-PRO-PRO-GLU-GLU-
                         *    *    |         *    *

THR-LEU-GLY-ASP-ASP-ARG-SER-LEU-ARG-SER-ASP-SER-SER-MET-
            LYS-LEU-ARG-ASP-ASP-ARG-SER-LEU-ARG-SER-ASP-SER-SER-VAL-
             *    *                                              *

ASN-SER-LEU-ASP-PHE-SER-SER-VAL-SER-ILE-VAL-ALA-LEU-ASN-
            ASN-LEU-LEU-ASP-VAL-PRO-SER-VAL-SER-ILE-VAL-ALA-LEU-ASN-
                 *    *        *    *

LYS-LYS-SER-LYS-LYS-ILE-SER-ARG-LYS-GLU-ALA-GLU-LYS-ARG-
            LYS-LYS-SER-LYS-GLN-ILE-GLY-ARG-LYS-ALA-ALA-GLU-LYS-LYS-
             |              *    *    *    *    *              *

LYS-ARG-SER-SER-LYS-LYS-LYS-ALA-SER-MET-LYS-LYS-VAL-ALA-
            ----ARG-SER-SER-LYS-LYS-GLU-ALA-SER-MET-LYS-LYS-VAL-VAL-
             *  ←  basic region  →  *                             *

ARG-PRO-PRO-PRO-PRO-SER-PRO-CYS-VAL-ALA-THR-ARG-ASP-SER-
            ARG-PRO-PRO-PRO-PRO-SER-PRO-CYS-VAL-ALA-THR-ASN-ASP-SER-
                                                          |

CYS-LYS-PRO-PRO-ALA-PRO-ALA-CYS-CYS-ASP-PRO-CYS-ALA-SER-
            CYS-LYS-PRO-PRO-ALA-PRO-ALA-CYS-CYS-ASP-PRO-CYS-ALA-SER-
                        ←  cysteine rich motif  →

CYS-GLN-CYS-ARG-PHE-PHE-GLY-SER-ALA-CYS-THR-CYS-ARG-VAL-
            CYS-GLN-CYS-ARG-PHE-PHE-GLY-ARG-ALA-CYS-SER-CYS-ARG-VAL-
                                         *         *

LEU-ASN-PRO-ASN-CYS-CO₂H  (SEQ ID NO:1)
            LEU-SER-LEU-ASN-CYS-CO₂H  (SEQ ID NO:2)
                 *   *
            *Difference
```

An agouti signaling peptide of the present invention is derived from a basic region or portion thereof, a cysteine rich region or portion thereof or a combination of a basic region and a cysteine rich region.

An agouti signaling peptide of the present invention is preferably no more than about 131 amino acid residues in length for reasons of ease of synthesis and ability to direct the inhibition. Thus, it is more preferred that an agouti signaling peptide be no more than about 109 amino acid residues, still more preferably no more than about 50 residues, and most preferably less than 20 amino acid residues in length. In one embodiment, an agouti signaling peptide of the present invention has about 5 to about 10 amino acid residues and has the ability to inhibit melanin production.

The invention is a purified biologically active peptide of the agouti signaling protein which has the following characteristics: (a) the peptide has depigmenting activity due to its ability to inhibit the production of at least one melanin; (b) the peptide has at least one region selected from the group consisting of: (i) at least one basic region derived from the full length agouti signaling protein or a portion thereof; and (ii) a cysteine rich region derived from the full length agouti signaling protein or a portion thereof; (c) the peptide has a minimum length of at least about 5 amino acid residues but has a maximum length selected from the group consisting of: (i) no more than about 131 amino acid residues; (ii) no more than about 109 amino acid residues; (iii) no more than about 50 amino acid residues; (iv) no more than about 20 amino acid residues; and (v) no more than about 10 amino acid residues; and wherein said agouti signaling protein is optionally coupled to a molecule which would facilitate its transport into cells. In a specific embodiment, the agouti signaling protein having these characteristics and a maximum length of no more than about 131 amino acid residues is provided. In a further specific embodiment, the agouti signaling protein has a maximum length of no more than about 109 amino acid residues.

In one embodiment, an agouti signaling peptide of the present invention has a length of no more than about 109 amino acid residues and includes an amino acid residue sequence or biologically active portion thereof represented by the formula:

His-Leu-Ala-Leu-Glu-Glu-Thr-Leu-Gly-Asp-Asp-Arg-Ser-Leu-Arg-Ser-Asp-Ser-Ser-Met-Asn-Ser-Leu-Asp-Phe-Ser-Ser-Val-Ser-Ile-Val-Ala-Leu-Asn-Lys-Lys-Ser-Lys-Lys-Ile-Ser-Arg-Lys-Glu-Ala-Glu-Lys-Arg-Lys-Arg-Ser-Ser-Lys-Lys-Lys-Ala-Ser-Met-Lys-Lys-Val-Ala-Arg-Pro (SEQ ID NO:3).

In another embodiment an agouti signaling peptide of the present invention has a length of no more than about 109 amino acid residues and includes an amino acid residue sequence or biologically active portion thereof represented by the formula:

His-Leu-Pro-Pro-Glu-Glu-Lys-Leu-Arg-Asp-Asp-Arg-Ser-Leu-Arg-Ser-Asp-Ser-Ser-Val-Asn-Leu-Leu-Asp-Val-Pro-Ser-Val-Ser-Ile-Val-Ala-Leu-Asn-Lys-Lys-Ser-Lys-Gln-Ile-Gly-Arg-Lys-Ala-Ala-Glu-Lys-Lys-Arg-Ser-Ser-Lys-Lys-Glu-Ala-Ser-Met-Lys-Lys-Val-Val-Arg-Pro (SEQ ID NO:4)

In another embodiment an agouti peptide of the present invention has a length of no more than about 109 amino acids, preferably less than about 50 amino acids, and includes an amino acid sequence or portion thereof represented by the formula:

> Pro-Pro-Pro-Ser-Pro-Cys-Val-Ala-Thr-Arg-Asp-Ser-Cys-Lys-Pro-Pro-Ala-Pro-Ala-Cys-Cys-Asp-Pro-Cys-Ala-Ser-Cys-Gln-Cys-Arg-Phe-Phe-Gly-Ser-Ala-Cys-Thr-Cys-Arg-Val-Leu-Asn-Pro-Asn-Cys (SEQ ID NO:5)

In another embodiment an agouti peptide of the present invention has a length of no more than about 109 amino acids, preferably less than about 50 amino acids and includes an amino acid sequence or portion thereof represented by the formula:

> Pro-Pro-Pro-Ser-Pro-Cys-Val-Ala-Thr-Asn-Asp-Ser-Cys-Lys-Pro-Pro-Ala-Pro-Ala-Cys-Cys-Asp-Pro-Cys-Ala-Ser-Cys-Gln-Cys-Arg-Phe-Phe-Gly-Arg-Ala-Cys-Ser-Cys-Arg-Val-Leu-Ser-Leu-Asn-Cys (SEQ ID NO:6)

In one embodiment, a preferred agouti signaling peptide includes at least one amino acid residue sequence or portion thereof represented by SEQ ID NO:3 or SEQ ID NO:4 and includes at least one amino acid residue sequence or portion thereof represented by SEQ ID NO:5 or SEQ ID NO:6 or combinations thereof.

Other exemplary peptides of the invention include but are not limited to peptides having an amino acid residue sequence selected from the group consisting of:

| | |
|---|---|
| His-Leu-Ala-Leu-Glu-Glu-Thr-Leu-Gly-Asp | (SEQ ID NO:7); |
| His-Leu-Pro-Pro-Glu-Glu-Lys-Leu-Arg-Asp | (SEQ ID NO:8); |
| Asp-Arg-Ser-Leu-Arg-Ser-Asp-Ser-Ser-Met | (SEQ ID NO:9); |
| Asp-Arg-Ser-Leu-Arg-Ser-Asp-Ser-Ser-Val | (SEQ ID NO: 10); |
| Asn-Ser-Leu-Asp-Phe-Ser-Ser-Val-Ile-Val | (SEQ ID NO: 11); |
| Asn-Leu-Leu-Asp-Val-Pro-Ser-Val-Ile-Val | (SEQ ID NO: 12); |
| Ala-Leu-Asn-Lys-Lys-Ser-Lys-Lys-Ile-Ser | (SEQ ID NO: 13); |
| Ala-Leu-Asn-Lys-Lys-Ser-Lys-Gln-Ile-Gly | (SEQ ID NO: 14); |
| Arg-Lys-Glu-Ala-Glu-Lys-Arg-Lys-Arg-Ser | (SEQ ID NO: 15); |
| Arg-Lys-Ala-Ala-Glu-Lys-Lys-----Arg-Ser | (SEQ ID NO: 16); |
| Ser-Lys-Lys-Lys-Ala-Ser-Met-Lys-Lys-Val | (SEQ ID NO: 17); |
| Ser-Lys-Lys-Glu-Ala-Ser-Met-Lys-Lys-Val | (SEQ ID NO: 18); |
| Ala-Arg-Pro-Pro-Pro-Ser-Pro-Cys-Val | (SEQ ID NO: 19); |
| Val-Arg-Pro-Pro-Pro-Ser-Pro-Cys-Val | (SEQ ID NO:20); |
| Ala-Thr-Arg-Asp-Ser-Cys-Lys-Pro-Pro-Ala | (SEQ ID NO:21); |
| Ala-Thr-Asn-Asp-Ser-Cys-Lys-Pro-Pro-Ala | (SEQ ID NO:22); |
| Pro-Ala-Cys-Cys-Asp-Pro-Cys-Ala-Ser-Cys | (SEQ ID NO:23); |
| Pro-Ala-Cys-Cys-Asp-Pro-Cys-Ala-Ser-Cys | (SEQ ID NO:24); |
| Gln-Cys-Arg-Phe-Phe-Gly-Ser-Ala-Cys-Thr | (SEQ ID NO:25); |
| Gln-Cys-Arg-Phe-Phe-Gly-Arg-Ala-Cys-Ser | (SEQ ID NO:26); |
| Cys-Arg-Val-Leu-Asn-Pro-Asn-Cys | (SEQ ID NO:27); |
| Cys-Arg-Val-Leu-Ser-Leu-Asn-Cys | (SEQ ID NO:28); | repeating sequences and combinations of one or more of the sequences thereof having the ability to inhibit the production of at least one melanin. The peptides may be screened for inhibitory activity using the methods described herein.

Due to the three dimensional structure of a native folded agouti signaling protein, multiple regions of agouti signaling protein may be involved in inhibiting melanin production. Thus, in another embodiment, the invention contemplates agouti signaling peptide compositions that comprise one or more of the different agouti signaling peptides described above, admixed in combinations to provide simultaneous inhibition of melanin. Similarly, mosaic polypeptides comprising two or more of the agouti signaling peptides, linked by other than the normal intervening amino acid sequences is also contemplated.

It should be understood that a subject peptide need not be identical to the amino acid residue sequence of SEQ ID NO: 1 or 2 so long as it includes the required sequence and is able to inhibit the production of at least one melanin as described herein.

A subject polypeptide includes any analog, fragment or chemical derivative of a polypeptide whose amino acid residue sequence is shown herein so long as the polypeptide is capable of inhibiting the production of at least one melanin. Therefore, a present polypeptide can be subject to various changes, substitutions, insertions, and deletions where such changes provide for certain advantages in its use.

The term "analog" includes any peptide having an amino acid residue sequence substantially identical to a sequence specifically shown herein in which one or more residues have been conservatively substituted with a functionally similar residue and which displays the ability to inhibit the production of melanin as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite inhibitory activity.

"Chemical derivative" refers to a subject peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and omithine may be substituted for lysine. Peptides of the present invention also include any peptide having one or more additions and/or deletions or residues relative to the sequence of a peptide whose sequence is shown herein, so long as the requisite activity is maintained.

The term "fragment" refers to any subject peptide having an amino acid residue sequence shorter than that of a polypeptide whose amino acid residue sequence is shown herein.

When a peptide of the present invention has a sequence that is not identical to the sequence of agouti signaling protein, it is typically because one or more conservative or non-conservative substitutions have been made, usually no more than about 30 percent, preferably no more than about 20 percent, and more preferably no more than about 10 percent of the amino acid residues are substituted. Additional residues may also be added at either terminus for the purpose of providing a "linker" by which the peptides of this invention can be conveniently affixed a carrier.

Carrier molecules may be used to provide stability to the peptide of the present invention and/or may be used to target the peptide to a particular site or a particular target cell. For example, the carrier may be a melanocyte receptor or melanocyte specific ligand that targets the agouti peptide to melanocytes. In another embodiment, the carrier is an auxiliary peptide which can facilitate delivery of the peptide to the target cells. An example of such a peptide is Penetratin sold by Appligene, a division of Oncor. The peptide is patented and has 16 amino acids. Other carrier molecules comprising peptides, sugars, lipids, etc. can be joined to the agouti signaling protein or peptides thereof to facilitate delivery to a target cell, improve stability or provide other useful functions.

In one embodiment a more stable derivative of the agouti signaling peptide is synthesized by protocols as described by Hadley, M. E. et al *Endocrine Res.* 11(3–4)157–170, 1985.

Amino acid residue linkers may be used to link the agouti peptide to the carrier molecule and are usually at least one residue and can be 40 or more residues, more often 1 to 10 residues. Typical amino acid residues used for linking are tyrosine, cysteine, lysine, glutamic and aspartic acid, or the like. In addition, a subject peptide can differ, unless otherwise specified, from the natural sequence of agouti signaling protein by the sequence being modified by terminal-$NH_2$ acylation, e.g., acetylation, or thioglycolic acid amidation, by terminal-carboxylamidation, e.g., with ammonia, methylamine, and the like.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

An agouti signaling peptide of the present invention, can be synthesized by any of the techniques that are known to those skilled in the polypeptide art, including recombinant DNA techniques. Methods for construction, expression and purification of recombinant proteins are detailed in: *Current Protocols in Molecular Biology,* Vols. 1–3, Eds. Ausubel, F. M. et al, John Wiley & Son, Inc., 1995. For producing short peptides, synthetic chemistry techniques, such as a solid-phase Merrifield-type synthesis, are preferred for reasons of purity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszly et al, "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above tests and in J. F. W. McOmie, "Protective Groups in Organic Chemistry", Plenum Press, New York, 1973, which is incorporated herein by reference.

The invention is a purified antibody that specifically binds a peptide of the invention. Particularly, the peptide can be a polyclonal antibody that specifically binds to a carboxy-terminal peptide having the sequence CGLGENSPLLS-GQQV (SEQ ID NO:24). In a further embodiment a purified monoclonal antibody that specifically binds the peptide having the sequence of SEQ ID NO:24. Purified polyclonal and monoclonal antibodies to other novel peptides of the invention are contemplated.

The present invention is a method of inhibiting at least one melanogenic enzyme, preferably inhibiting more than one melanogenic enzyme. Because the skin pigmentation genes cloned thus far show high levels of sequence similarity and have the same functions between mice and humans, the results of the experiments on mice are clearly correlated to expected results in humans. Melanogenic enzymes which may be inhibited or down-regulated include but are not limited to tyrosinase, TRP1 and human homolog thereof, TRP2 and human homolog thereof and the like.

In one embodiment of the invention the method of inhibiting or down-regulating a melanogenic enzyme results in inhibition of tyrosinase, TRP1 and TRP2. Thus a method of down-regulating in a subject a melanogenic enzyme involved in melanin synthesis, comprising administering to the subject an amount of the agouti signaling protein or a biologically active peptide thereof to down-regulate the melanogenic enzyme is provided. In another embodiment of the invention the method results in inhibition of the synthesis of at least one melanin. Such melanins which may be inhibited by the present invention include but are not limited to eumelanin and pheomelanin. In a preferred embodiment the method results in the inhibition of production of at least eumelanin.

The method is the administration of agouti signal protein or one or more biologically active peptides thereof to a mammal in an amount sufficient to inhibit or decrease the production or synthesis of at least one melanin, for example, eumelanin and pheomelanin.

The present method is particularly useful in the treatment of hyperpigmentation conditions or diseases which include but are not limited to melasma, photoaging spots, solar keratosis, post-inflammatory hyperpigmentation, and the like.

Agouti signaling protein and biologically functional peptides thereof are useful in methods of inhibiting melanin production at a site of hyperpigmentation in a mammal, preferably a human. Agouti signaling protein or biologically functional peptide thereof administered at such sites prevents or inhibits the formation of melanin at the site. Thus, the invention is a method of reducing melanin synthesis in a subject, comprising administering to a subject in need of such reduction an amount of the agouti signaling protein or a biologically active peptide thereof to reduce melanin synthesis.

In the method of treatment, the administration of agouti signaling protein or biologically functional peptides thereof may be provided for either prophylactic or therapeutic use. When provided prophylactically, the agouti signaling protein or biologically functional peptides thereof is provided in advance of any overproduction of melanin at a site. The prophylactic administration of the protein or peptides of the present invention serves to prevent or inhibit any melanin overproduction at the site. When provided therapeutically, the protein or peptide is provided at (or after) the onset of melanin production at a site. Thus, the protein or peptide may be provided either prior to the anticipated melanogenesis at the site or after melanogenesis has begun at a site.

The term "unit dose" as it is used herein refers to physically discrete units suitable as unitary dosages for mammals, each unit containing a predetermined quantity of agouti signaling protein, peptides and derivatives thereof calculated to produce the desired inhibitory effect.

The inoculum is typically prepared as a solution in tolerable (acceptable) diluent such as saline, phosphate buffered saline or other physiologically tolerable diluent and the like to form an aqueous pharmaceutical composition. In addition, the protein, peptides and derivatives thereof may be formulated in solid form and lyophilized form and redissolved or suspended prior to use.

The composition may optionally contain other therapeutics. Of particular interest are therapeutics useful in the prevention or treatment of damaged skin. For example, the composition may also comprise estrogen or derivatives thereof, tretinoin or Vitamin A derivatives, UV-A and/or UV-B sun-blocking agents, antibiotics, acne treatment agents, and the like. For example, the composition may comprise an effective concentration of agouti signaling peptide in combination with an effective concentration of tretinoin formulated as a cream. The concentration of tretinoin may be from about 0.025% to about 0.1% tretinoin.

The agouti signaling protein or peptides may also be formulated into a cosmetic composition.

The route of administration may be subcutaneous (S.C.), intradermal (I.D.), topical and the like so as to be directed to melanocytes. One embodiment of the method of treatment the protein, peptide or derivatives thereof are administered topically. The peptides of the present invention may be modified by the addition of a carrier group that facilitates their penetration through the skin. Such groups include but are not limited to lipophilic groups and the like. Examples of lipophilic groups are fatty acids or fatty alcohols in addition to long chain hydrocarbyl groups. Other formulations for enhancing epidermal, dermal and transdermal penetration of topically applied pharmacologically active agents is disclosed in U.S. Pat. Nos. 5,326,566, 5,409,917 and 5,260,292. Alternatively, the peptides of the present invention may be formulated into liposomes to facilitate their entry using topical administration. For topical administration, the protein, peptide or derivatives thereof is formulated into ointments, salves, gels, dermal patches or creams, as is generally known in the art.

In providing a mammal, preferably a human, with the agouti signaling protein or peptide, the dosage of administration of the protein, peptides or derivatives thereof will vary depending upon such factors as the mammal's age, weight, height, sex, general medical condition, previous medical condition, route of administration, formulation and state of progression of the hyperpigmentation.

In general, it is desirable to provide the recipient with a dosage of agouti signaling protein or peptide of at least about picomolar concentrations, preferably at least about nanomolar concentrations, although a lower or higher dose may be administered. In the case of stable derivatives with long half-lives, lower doses may be effective such as, but not limited to, a picomolar range. The dose provides an effective tissue level of agouti signaling protein or peptides thereof for inhibiting melanogenesis at a site. The dose is administered at least once. Multiple administration over a period of hours, days or weeks may be preferable. It may also be preferable to administer the protein or peptide at least once/week and even more frequent administrations. Subsequent doses may be administered as indicated.

In one embodiment the agouti signaling protein or peptides thereof in provided topically in the form of a lotion that is applied to the affected skin of the hands and face on a daily basis.

The methods described herein are useful in screening analogs, derivatives and fragments of the agouti signaling protein for those useful in inhibiting melanogenesis. In the method, an amount of an agouti protein or peptide is added to cultured primary melanocytes or melanocyte cell lines. At various time intervals, samples are removed and the amount of melanocyte enzyme determined. Thus, the invention is a method of screening for inhibitors of melanin synthesis, comprising: a) contacting a melanocyte culture with an amount of a putative inhibitor of melanin synthesis; b) determining the amount of melanocyte enzyme present in the melanocyte culture from step a); c) comparing the amount of melanocyte enzyme determined in step b) to the amount of melanocyte enzyme in an uncontacted melanocyte culture; and d) correlating a decrease in at least one melanocyte enzyme with an inhibitor of melanin synthesis. A decrease in at least one melanocyte enzyme compared to a control is indicative of an inhibitory agouti protein or peptide.

There are genetic conditions that result in over-expression of agouti signaling protein. One example is the lethal yellow mutation in mice. Other conditions or diseases such as melasma photoaging spots, solar keratosis, and post-inflammatory hyperpigmentation such as occurs at sites of wound healing are related to the over-expression of a melanin. Thus another aspect of the invention is the modulation of expression of endogenous agouti signaling protein in a mammal. Expression of endogenous agouti signaling protein may be inhibited at the protein level by agents such as anti-agouti signaling protein antibody, FAb fragments and the like or by chemical agents that bind to the agouti protein thus preventing its function.

At the transcription or translation level, anti-sense oligonucleotides may be used to prevent the expression of the agouti signaling protein. Such anti-sense oligonucleotides are formulated based on the nucleic acid sequence encoding the protein of SEQ ID NO:1 or SEQ ID NO:2 and can be made by methods known in the art. Thus, the invention includes a method of altering melanin synthesis in a subject, comprising administering to the subject an amount of a nucleic acid that hybridizes to a nucleic acid encoding an agouti signaling protein, whereby the agouti encoding nucleic acid is not transcribed or translated and melanin synthesis is altered. This treatment results in enhanced eumelanogenesis, which can be beneficial in treating vitiligo, leucoderma, some forms of albinism and hair graying.

This technique can be antisense RNA therapy. The general protocol is to identify the gene that causes disease in humans. The agouti signaling protein-encoding gene is such a gene. Next, the gene is cloned (Bultman et al., 1992 and Miller et al., 1993), but in a reverse orientation and with an powerful inducible exogenous promoter. This construct is then integrated into a cell that expresses the gene, the promoter is activated by an inducing compound, and "antisense" RNA in produced. This RNA is capable of binding to "sense" RNA (e.g., mRNA) that is produced in the disease state. By blocking the sense RNA, translation is prevented, and the product's effect in causing disease is halted.

To get the antisense molecules into the target cells a carrier molecule will be covalently linked to the antisense molecule. This carrier moiety will take the form of a necessary/required biochemical compound for the agouti signaling protein-expressing cells. The cell will be tricked into accepting the carrier molecule and, thus, the entire antisense molecule. Binding kinetics will take over form this point. In the case of antisense DNAs, much smaller numbers of anti-ASP molecules should be required to shut down transcription, perhaps translation, and ultimately impact melanin production.

It is understood that the examples and embodiments described herein are for illustrative purposes only and that various modifications or changes in light thereof will be suggested to persons skilled in the art and are to be included within the spirit and purview of this application.

All references and patents referred to are incorporated herein by reference.

EXAMPLE 1

Materials and Methods

Animals

C3H/HeJ agouti mice (A/A:B/B:C/C) and C57BL/6J (C3H/HeJ F12 mice (A/a:B/B:C/C) were purchased from Charles River (Kingston, N.Y.). C57BL/6J nonagouti black mice (a/a:B/B:C/C) and C57BL/6J lethal yellow mice (A/a:B/B:C/C) were obtained from Jackson Laboratory (Bar Harbor, Me.). Lethal yellow mice were maintained by matings between heterozygous lethal yellow (A/a) male and black (a/a) female mice. Sibling nonagouti (a/a) and heterozygous (a/a) mice and female C57BL/6J (C3/HeJ F1 (A/a) mice. All mice were housed in the animal facility of NCI/HIH.

Antibodies Used

Antibodies used in this study were generated in rabbits against synthetic peptides corresponding to the unique carboxyl sequence of the four melanogenic proteins studied; their specificities have been thoroughly detailed in the appropriate references. They are termed αPEP1 (which recognizes TRP1; Jimenez et al., 1991), αPEP7 (which recognizes tyrosinase; Jimenez et al., 1991), αPEP8 (which recognizes TRP2; Tsukamoto et al., 1992) and αPEP13 (which recognizes the silver protein; Kobayashi et al, 1994a).

Sample Preparation

Anesthetized mice were killed by cervical dislocation, and their dorsal skins were cleaned with 60% ethanol and dissected. Immediately after removing fat tissue, the dorsal skins were homogenized in 5 volumes (v/v) of NP40/SDS buffer (1% Nonidet P-40, 0.01% SDS, 0.1 M Tris HCl, pH 7.2 1 µg ml aprotinin and 100 µM phenylmethylsulfonyl fluoride) on ice using a Potter-Elvehjem glass homogenizer, or they were frozen and kept at −70° C. until use. Following centrifugation at 1,000 g for 10 minutes at 4° C., the supernatant was subsequently centrifuged at 10,000 g for 30 minutes at 4° C. The supernatant was filtered through a 0.45 µm pore filter unit (Millex, Millipore Co., Bedford, Mass.) and the soluble skin extracts were used for menalogenic assays and western immunoblotting analyses, as detailed below. In some cases where noted, hair bulbs were collected from dorsal skins using razor blades.

Organ Culture

This technique was carried out as previously described (Imokawa et al., 1988). Briefly, dorsal skins were excised from 6- or 10-day-old mice, cleaned to remove the fat tissue and to expose the hair bulbs, and were then cut into pieces (~1 mm×2 mm) using razor blades. The pieces were sterilized in Hanks' balanced salt solution containing 400 i.u./ml penicillin and 400 µg/ml streptomycin for 20 minutes, and then placed on sheets of lens paper over stainless steel grids in organ culture dishes (Falcon 3037, Lincoln Park, N.J.). A 750 µl sample of Dulbecco's modified Eagle's medium, containing 10% fetal bovine serum, 100 i.u./ml penicillin and 100 µg/ml streptomycin, were added to the inner plates of the dishes in order to culture the skin tissue at the liquid/air (5% $Co_2$) interface at 37° C.

Cells and Culture Conditions

The melan-a melanocyte cell line cultured from genetically defined C56B1 mice (a/a B/B C/C) was a kind gift from Dr. Dorothy Bennett, London, United Kingdom. The cells were grown as initially reported (Bennett et al., 1987).

Metabolic Labeling and Immunoprecipitation

These techniques were performed as previously reported (Jimenez et al., 1989, 1991; Tsukamoto et al., 1992; Aroca et al., 1993; Kobayashi et al., 1994a). Briefly, dorsal skin fragments in organ culture were preincubated for 1 hour in methionine-free medium containing dialyzed fetal bovine serum, and labeled for 4 or 6 hours with [$^{35}$S]methionine (0.4~1.0 mCi/ml) (Dupont-NEN, Boston, Mass.) in methionine-free medium. They were washed three times with ice-cold $Ca^{2+}$, $Mg^{2+}$-free phosphate buffered saline (PBS-), containing excess unlabeled methionine, and the hair bulbs were collected from radiolabeled skin pieces using razor blades; these were homogenized and lysed overnight at 4° C. in NP40/SDS buffer, as detailed above. The lysates were then centrifuged for 30 minutes at 10,000 g, and the supernatants were then precleared with normal rabbit serum and GammaBind G Sepharose (Pharmacia/LKB, Piscataway, N.J.). A sample containing $10^7$ TCA-precipitable cpm of the precleared extracts was incubated with 5 µl of the antibodies noted in the Figure legends for 1 hour at 4° C., and then complexed with 30 µl; GammaBind G Sepharose for 30 minutes at 4° C. The immune complexes were washed 5 times with NP40/SDS buffer, then eluted in SDS sample buffer at 95° C. for 5 minutes and analyzed by SDS-gel electrophoresis (Laemmli, 1970), followed by fluorography.

Western Immunoblotting Analysis

This technique was also performed as reported previously (Jimenez et al., 1991; Aroca et al., 1993; Kobayashi et al., 1994a). Briefly, proteins from NP40/SDS-solubilized melan-a cells or dorsal skins were separated on 7.5% SDS gels, then transferred to polyvinylidene difluoride membranes (Immunobilon-P, Millipore Corp., Bedford, Mass.) and incubated with primary antibodies (1/1000 dilution) as noted in the Figure legends. Subsequent visualization of antibody binding was carried out with Enhanced ChemiLuminescence (Amersham Corp., Arlington Height, Ill.) according to the manufacturer's instructions.

Melanogenic Assays

Assays for melanogenic catalytic activities as described below were carried out at pH 6.8, 37° C. for 60 minutes. (1)

Tyrosine hydroxylase activity was measured using the [$^3$H] tyrosine assay (Hearing and Ekel, 1976; Hearing, 1987). This method specifically measures the tritiated water produced during the hydroxylation of tyrosine to DOPA. (2) DOPA oxidase activity was measured using incorporation of [3-$^{14}$C]DOPA into acid-insoluble melanin as detailed previously (Aroca et al., 1993). (3) DOPAchrome tautomerase activity was measured by HPLC as the disappearance of DOPAchrome substrate and the production of DHICA rather than DHI; data are converted to pmol products by comparison with known standards. The HPLC assay was detailed previously (Palumbo et al., 1987; Tsukamoto et al., 1992). (4) DHI oxidase and DHICA oxidase activities were measured by HPLC as the disappearance of these substrates from reaction mixtures compared to controls for spontaneous auto-oxidation; data are converted to pmol by comparison with known standard (Aroca et al., 1993). (5) Melanin production was measured using incorporation of [$^{14}$C] tyrosine into acid-insoluble melanin, also as detailed previously (Hearing and Ekel, 1976; Hearing, 1987); pmol melanin produced are calculated from the radioactive product.

Tyrosine and DOPA used as standards and reaction substrates in these assays were obtained from Sigma Chemical Co. (St. Louis, Mo.); [L-3,5-$^3$H]tyrosine, [3-$^{14}$C]DOPA and [U-$^{14}$C]tyrosine were obtained from New England Nuclear (Boston, Mass.); DOPAchrome was prepared using the silver oxide method originally described by Korner and Pawelek (1980). DHI and DHICA were kindly provided by Dr. Giuseppe Prota (University of Naples, Naples) and Dr. Shosuke Ito (Fujita Health University, Nagoya) and purchased commercially from Regis Chemical Co. (Morton Grove, Ill.).

RNA Isolation and Northern Blotting

These techniques were performed as described previously (Aroca et al., 1993). Briefly, 2.0 μg of mRNA, isolated using a total RNA isolation kit and mRNA purification kit (Promega, Madison, Wis.), were electrophoresed and then blotted to Sure-Blot nylon membranes (Oncor, Gaithersburg, Md.), hybridized with $^{32}$P-labeled probes, dehybridized and rehybridized with other probes again as necessary. TYRS-J, the probe specific for tyrosinase, was kindly provided by Drs. H. Yamamoto and T. Takeuchi, Sendai, Japan and is described in Yamamoto et al *Japan J. Genetics* Vol 62:271–274, 1987. pMT4, specific for TRP1, was provided by Dr. S. Shibahara, Sendai, Japan and is described in Shibahara, S. et al *Nucleic Acid Res.* Vol 14:2413–2427, 1986. TRP2a, specific for TRP2 was provided by Dr. I. Jackson, Edinburgh, Scotland and is described in Jackson, I et al. *EMBO* Vol 11:527–535, 1992. gp100, specific for silver, was provided by Dr. Y. Kawakami, Bethesda, Md. and is described in Kawakami et al *PNAS*, Vol. 91, 6458–6462, 1994.

Miscellaneous Methods

Protein concentrations were determined with the BCA assay kit (Pierce Chem Co., Rockford, Ill.) using bovine serum albumin as the standard. Quantitation of western blots and autoradiographs was performed using ImageQuant imager and software.

EXAMPLE 2

Melanogenic Protein Expression in Hair Bulbs of Newborn Lethal Yellow and Black Mice The expression of melanogenic proteins during pheomelanogensis was studied by comparing dorsal hair bulbs of 10 day newborn lethal yellow and black mice; these were sibling offspring from the same litter. Ten days newborn lethal yellow mice produce predominantly pheomelanin in their hair bulb although younger lethal yellow mice make minor amounts of eumelanin and brownish pigment can occasionally be observed in their hair bulbs.

The three distinct tyrosinase activities (i.e. tyrosine hydroxylase, DOPA oxidase and DHI oxidase), as well as the ability to produce melanin in extracts of hair bulbs from lethal yellow mice were about 20–25% the levels found in extracts of hairbulbs from the black sibling mice (Table 1). However, levels of DOPAchrome tautomerase activity (i.e. TRP2) and DHICA oxidase activity (i.e. TRP1) in these extracts of pheomelanogenic hair bulbs were at background levels. The relatively higher specific activities of these catalytic functions measured in pure population of melan-a melanocytes are shown for comparison.

TABLE 1

Melanogenic activities hair bulbs from newborn lethal yellow and black mice

| Sample | Tyrosine hydroxylase | DOPA oxidase | DOPA chrome tautomerase | DHI oxidase | DHICA oxidase | Melanin formation |
|---|---|---|---|---|---|---|
| Lethal yellow | 12 ± 4 (n = 5) | 150 ± 57 (n = 5) | 0.3 ± 0.6 (n = 6) | 23 ± 7 (n = 5) | −10 ± 17 (n = 3) | 3 ± 1 (n = 5) |
| Black | 46 ± 21 (n = 5) | 538 ± 270 (n = 5) | 93 ± 72 (n = 6) | 131 ± 83 (n = 5) | 21 ± 31 (n = 3) | 10 ± 6 (n = 5) |
| Melan-a | 110 ± 13 (n = 3) | 1039 ± 13 (n = 3) | 114 ± 60 (n = 3) | 432 ± 140 (n = 7) | 319 ± 111 (n = 7) | 33 ± 6 (n = 7) |

Hair bulbs from 10 day newborn lethal yellow and black sibling mice (or melan-a cells in culture) were solubilized and assayed for melanogenic activities, as detailed in Materials and Methods. Data are reported as means ± s.e.m. in pmol/mg protein per hour; n = number of independent experiments.

Figure 2:
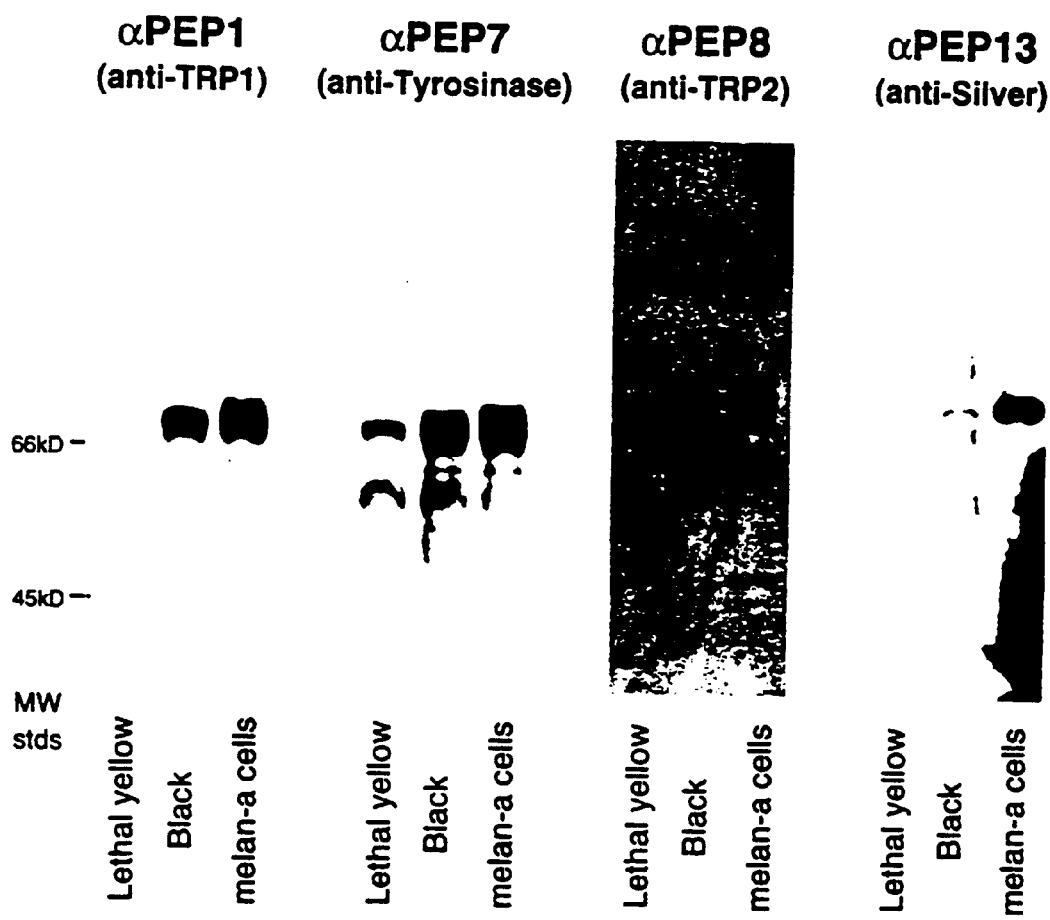
FIG. 2 shows analysis of melanogenic proteins expressed by hair bulb melanocytes of newborn lethal yellow and black mice. A 20 μg sample of protein from extracts of hair bulbs of 10 day newborn lethal yellow or black mice (or melan-a cells) were electrophoresed in SDS/polyacrylamide gels, transferred to membranes and analyzed for melanogenic proteins by western immunoblotting, as detailed in Materials and Methods. Skin tissues in organ culture (or melan-a cells) were labeled with [$^{35}$S]methionine for 4 hours, solubilized and immunoprecipitated by antibodies noted, separated by SDS-PAGE, dried and fluorographed, as detailed in Materials and Methods.

By western immunoblotting analysis, the patterns of expression of tyrosinase, TRP1 and TRP2 were consistent with the results of melanogenic assays (FIG. 2). Extracts of hair bulbs derived from newborn black mice had all four melanosomal proteins (tyrosinase, TRP1, TRP2 and the silver protein) with the same molecular mass as found for the melan-a murine melanocyte line used as a positive control. However, a significantly lesser amount of tyrosinase was detected in hair bulbs derived from newborn lethal yellow mice, and TRP1, TRP2 and the silver protein were undetectable in those pheomelanic hair bulbs. Metabolic labeling with [$^{35}$S]methionine followed by immunoprecipitation analysis of dorsal hair bulbs grown in organ culture showed similar patterns for synthesis of melanogenic proteins by lethal yellow and black melanocytes (data not shown). In hair bulbs derived from black mice, tyrosinase, TRP1 and TRP2, as well as the silver protein, were detectable and comparable in size to those found in the melan-a cells. However, in hair bulbs derived from lethal yellow mice, significantly decreased tyrosinase synthesis was detected, and there was no significant expression of TRP1, TRP2 or the silver protein.

Figure 3:
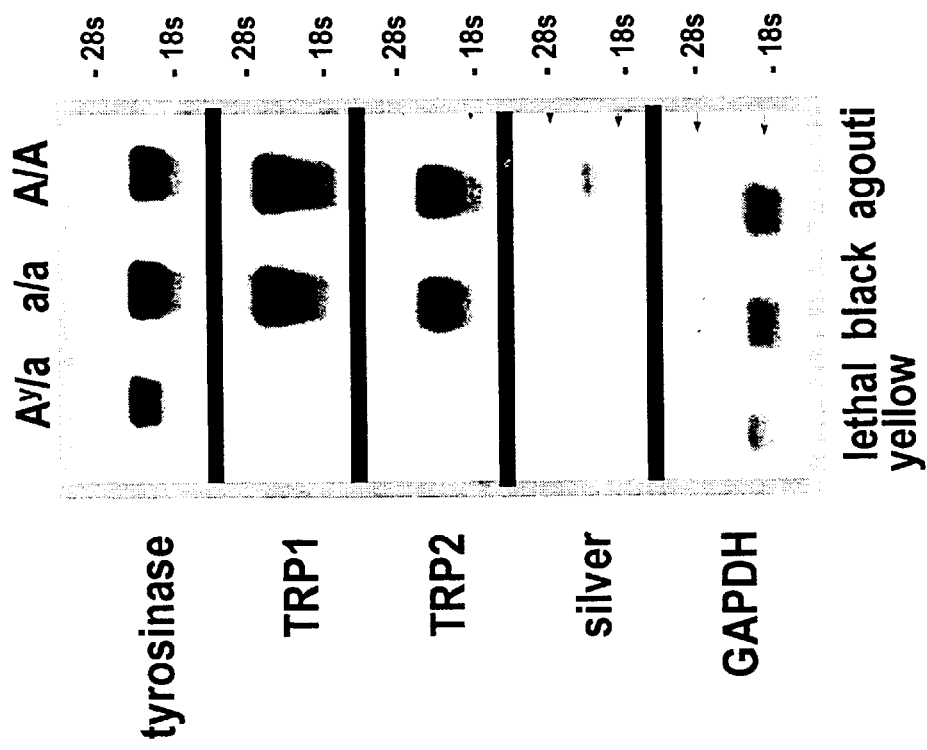
FIG. 3 shows Northern blot analysis of RNAs present in hair bulb melanocytes of newborn lethal yellow, black and agouti mice. mRNAs from hair bulbs of 10 day newborn lethal yellow, black and agouti mice were isolated and electrophoresed (2 μg/lane), transferred to nylon membranes and repeatedly hybridized with $^{32}$P-labeled probes for tyrosinase, TRP1, TRP2 and silver protein or GAPDH (glyceraldehyde-3-phosphate dehydrogenase), as detailed in Materials and Methods. s, Svedberg units.

Northern blot analysis confirmed that the pheomelanogenic hair bulbs of lethal yellow mice produced only tyrosinase mRNA but little or no mRNA for TRP1, TRP2 or the silver protein, although we could readily detect significant levels of mRNAs for all of those melanogenic proteins in the eumelanogenic hair bulbs obtained from black or agouti mice (FIG. 3).

Taken together, these results at the enzyme activity, translational and transcriptional levels, show clearly that tyrosinase function is reduced in hair bulbs of newborn lethal yellow mice while TRP1, TRP2 and the silver protein are not expressed at all. Therefore, the functions of TRP1, TRP2 and the silver protein cannot be essential for pheomelanogenesis.

was not detected in any of these skin extracts by western blotting (not shown). Assays for tyrosine hydroxylase and DOPAchrome tautomerase activities in those same extracts showed results consistent with the western immunoblotting analysis (Table 2).

The levels of DHICA production in crude extracts of tissues is occasionally significantly above background; this high background (~5–6 pmol in this experiment) is presumably due to the presence of divalent metal cations in these crude samples, which can catalyze this tautomerase reaction in the absence of active enzyme, as noted above.

TABLE 2

Melanogenic activities in skin extracts of newborn agouti and black mice

|   | Age (days) | Tyrosine hydroxylase | DOPA oxidase | DOPA chrome tautomerase | DHI oxidase | DHICA oxidase | Melanin formation |
|---|---|---|---|---|---|---|---|
|   |   |   | Experiment 1 |   |   |   |   |
| agouti | 5 | 40 | 33 ± 1 | 3 ± 0 | 39 | 9 | 0.5 ± 0.0 |
| agouti | 11 | 3 ± 0 | 24 ± 1 | 8 ± 0 | 46 | 16 | 0.4 ± 0.0 |
|   |   |   | Experiment 2 |   |   |   |   |
| agouti | 5 | 6 ± 0 | 63 ± 1 | 5 ± 0 | 31 | 2 | 1.1 ± 0.1 |
| black | 5 | 10 ± 0 | 114 ± 2 | 9 ± 0 | 37 | 13 | 2.4 ± 0.1 |

Hair bulbs from dorsal skins of 5 days and 11 days newborn agouti mice (top) and from dorsal skins of 5 days newborn agouti and black sibling mice (bottom) were solubilized and assayed for melanogenic activities, as detailed in Materials and Methods. Data are reported as means ± s.e.m. in pmol/mg protein per hour.

EXAMPLE 3

Figure 4:
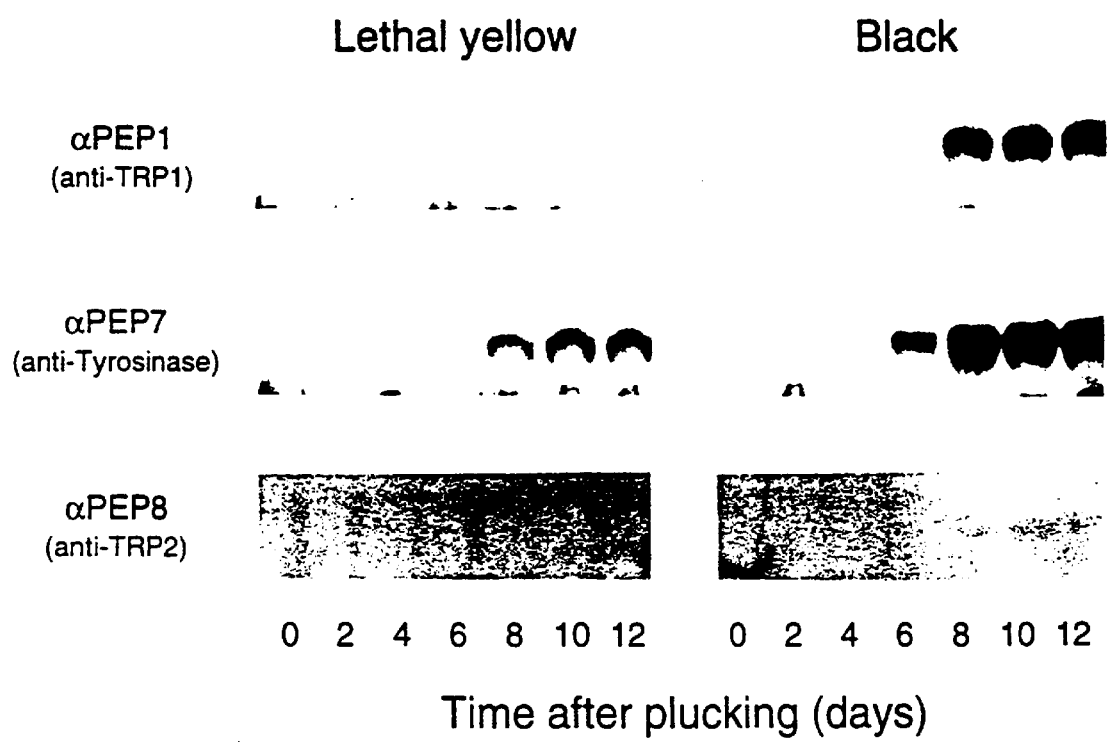
FIG. 4 shows expression of melanogenic proteins in regenerating hair bulbs of lethal yellow and black mice. Anagen growth hairs were induced by plucking the dorsal telogen hairs of 2-month-old sibling lethal yellow and black mice. Seven 1 cm×1 cm squares on each mouse were randomly plucked at 0 (immediately before), 2, 4, 6, 8, 10 and 12 days before sacrifice. Dorsal skin samples were collected from 3 mice of each genotype, solubilized and analyzed by western immunoblotting, as detailed for FIG. 2; 30 μg protein was separated in each lane.

Expression of Melanogenic Proteins in Regenerating Hair Bulbs of Lethal Yellow and Black Adult Mice To examine whether similar patterns of melanogenic proteins were expressed in regenerating hair bulbs of adult mice, anagen growth of hairs was induced by plucking the dorsal telogen hairs of 2-month-old lethal yellow and black sibling mice. Regenerating hairs on the dorsa could be observed 10 days after plucking in both types of mice and hair growth in both genotypes occurred at identical rates. Pieces of the regenerating dorsal skin were biopsied, homogenized, solubilized in NP40/SDS buffer and then analyzed by western immunoblotting and melanogenic enzyme assays. The expression of tyrosinase, TRP1 and TRP2 could be detected in regenerating hair bulbs of black mice by western immunoblotting as early as 6 days after plucking (FIG. 4). The levels of each of those proteins increased further at 8 and 10 days post-plucking and remained constant at 12 days. However, expression of TRP1 and TRP2 could not be detected in the regenerating pheomelanic hair bulbs of sibling lethal yellow mice at any time up to 12 days post-plucking, although a reduced expression of tyrosinase (compared to the black controls) was seen during this same time period. The silver protein

EXAMPLE 4

Figure 5:
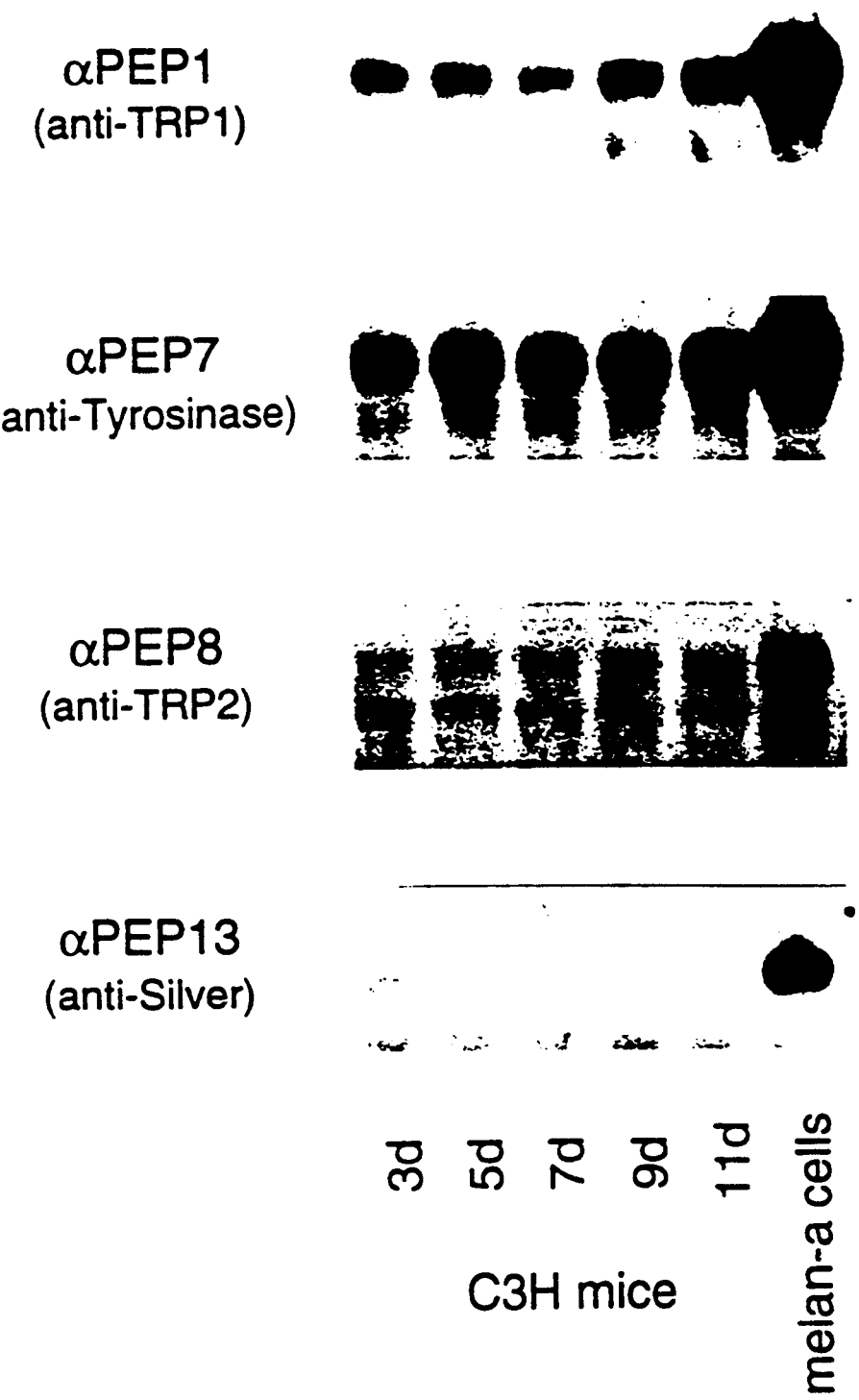
FIG. 5 shows expression of melanogenic proteins in dorsal skins of newborn agouti (A/A) mice. Dorsal skins were collected from 3, 5, 7, 9 and 11 day newborn agouti mice, solubilized and analyzed by western immunoblotting, as detailed for FIG. 2; 30 μg protein of each dorsal skin extract (10 μg of the melan-a cell extract) were separated in each lane.

Patterns of Melanogenic Protein Expression During the Physiological Switch from Pheo- to Eumelanogenesis C3H agouti mice have the typical agouti hair pattern, i.e. a yellow strips in two regions of the black background on each hair shaft. This pattern is generated by temporarily switching the type of melanin formed from eumelanin to pheomelanin and then back to eumelanin again during hair growth. The expression of melanogenic proteins in agouti hair bulbs before, during and after their pheomelanic phase was investigated to determine if down-regulation of TRP1, TRP2 and silver protein expression occurred physiologically as had been observed above in regenerating hair bulbs of lethal yellow mice. Western immunoblotting (FIG. 5 and quantitation of those blots) revealed a decrease (maximal at day 7) in the expression of TRP1 in follicular melanocytes of newborn agouti mice, exactly the time at which pheomelanin is produced predominantly. This can be compared with the eumelanogenic stage (at 9 and 11 days), at which levels of TRP1 increase; it can be seen that the amount of tyrosinase present in those tissues was relatively constant throughout this same time frame. Results consistent with these patterns of expression were obtained in melanogenic assays (Table 2, top), where levels of tyrosinase activities were comparable in extracts of 5 day and 11 day newborn agouti skins, whereas the catalytic activity of TRP1 (DHICA oxidase) at day 5 was significantly less (only about 50%) than that detectable at day 11. Although there was no significant decrease in the TRP2 band detected by western blot (FIG. 5), its catalytic function (DOPAchrome tautomerase) was decreased ~50% at day 5 compared to day 11.

Figure 6B:
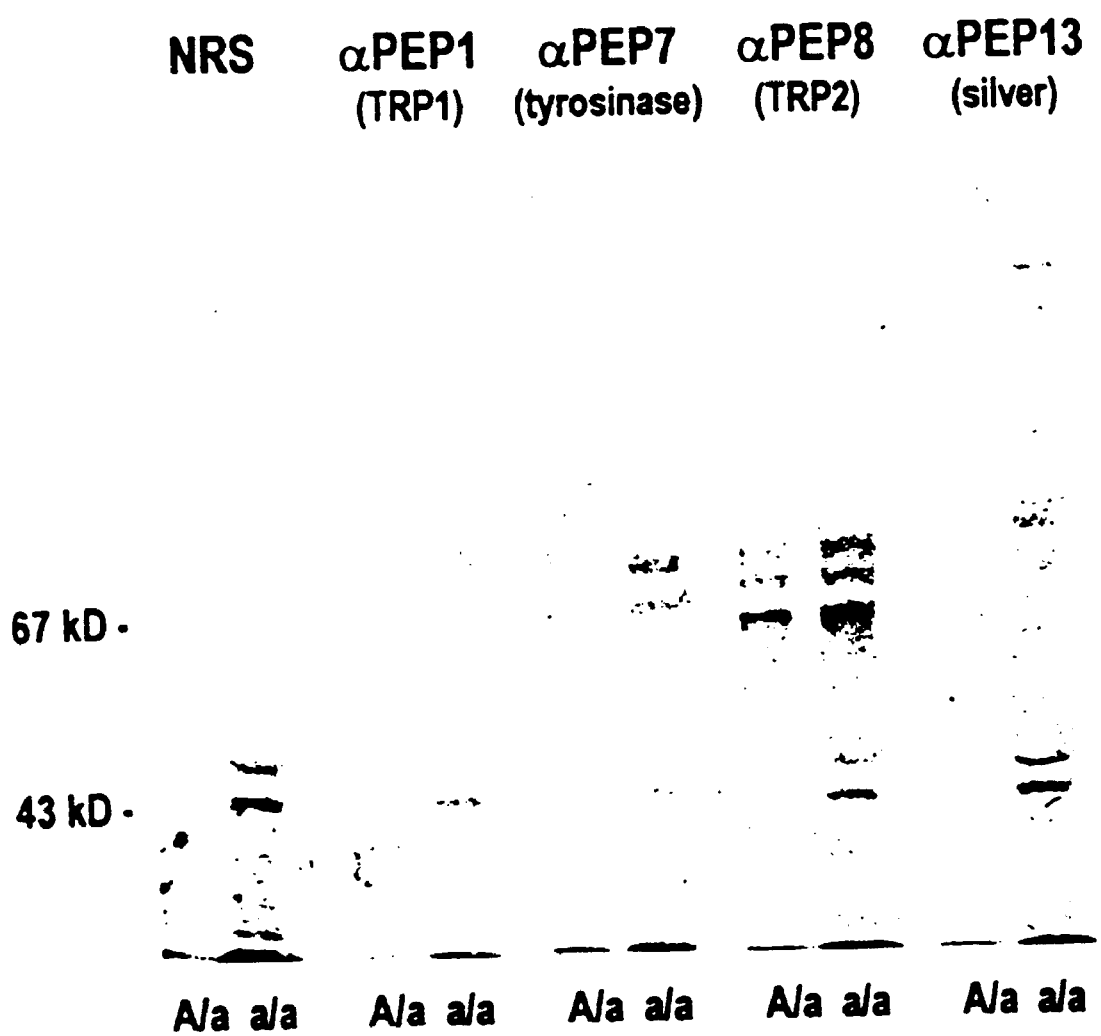

The expression of these melanogenic proteins in hair bulbs of sibling 5 day and 11 day newborn heterozygous agouti (A/a) and homozygous nonagouti (a/a) black mice were also examined. Results similar to those described above were obtained by western immunoblotting analysis (FIG. 6A) and by melanogenic assays (Table 2, bottom); that is, expression of tyrosinase and TRP2 was relatively constant in both genotypes at day 5 and day 11, whereas expression of TRP1 was reduced ~50% during the pheomelanogenic phase (day 5) in the agouti hair bulbs. In the experiments shown in FIGS. 5 and 6A, the silver protein was not detected by western blotting due to its low concentration in these extracts. Therefore expression of the silver pattern using metabolic labeling and immunoprecipitation of organ culture of skin obtained from 5-day old agouti and black sibling mice (FIG. 6B) was examined. Those experiments demonstrated that, as found for TRP1, there was significantly less of the silver protein synthesized in hair bulbs of 5-day-old agouti mice compared to hair bulbs from black mice.

EXAMPLE 5

Agouti Protein Suppresses Expression and Activity of Tyrosinase and Tyrosinase-related Protein in Murine Melanocytes To characterize the switch between eumelanogenesis and pheomelanogenesis, the responses of cultured melanocytes exposed to αMSH and/or agouti were determined.

The melan-a melanocyte cell line was used as described in Example 1. This clonal line was derived from C57B1 nonagouti black mice. The growth medium was minimum essential medium containing 200 nM TPA. B16F10 melanoma cells were also used to compare the effect of agouti protein with melan-a. These cells were grown in Dulbecco's modified Eagle medium.

Recombinant agouti protein was purified from baculovirus system by Dr. Michael Ollmann in Dr. Gregory Barsh's laboratory by methods known in the art. $2 \times 10^6$ cells were seeded per 15 cm diameter dish. The medium was changed everyday, and fresh agouti protein and/or αMSH added everyday usually at 10 nM. To examine transcriptional regulation, total RNA was isolated and Northern blotting performed by methods described in Example 1. The A26 probe to the MSH-R was provided by Dr. R. Cone and is described in Mountjoy et al. *Science* 257:1248–1251, 1992. At the translational level, metabolic labeling was used in conjunction with immunoprecipitation as described in Example 1. Western blotting and enzyme assay was used to examine function.

First, it was determined whether the agouti protein had any effect on tyrosinase expression by Northern blotting. Melan-a cells were treated with 4 concentrations of agouti protein as indicated in FIG. 7A. After 24 hours, the cells were harvested, total RNA isolated and hybridized with a probe for tyrosinase and detected by a phosphoimager. The activity of each band was measured by phosphoimager and the % control was corrected using GAPDH as a standard. Though the incubation time was only 24 hours, there were significant dose dependent decreases in expression of tyrosinase at 10 nM and 1 nM of agouti protein. It should be noted that in vivo, pheomelanin is synthesized within 24 hours after agouti RNA is apparent. Longer incubation times were also examined. 10 nM of agouti protein was added for 1, 2 or 4 days. After 2 or 4 days incubation, the decreases in expression of tyrosinase were much more dramatic, resulting in complete inhibition by day 2 (FIG. 7B).

After 5 days incubation of melan-a cells with 10 nM agouti protein, the color of pellet was changed from black to light brown. By ultrastructural study, after exposure to agouti protein, the amount of melanosomes were decreased and pheomelanosome-like structures were found (FIG. 8B).

Figure 9:
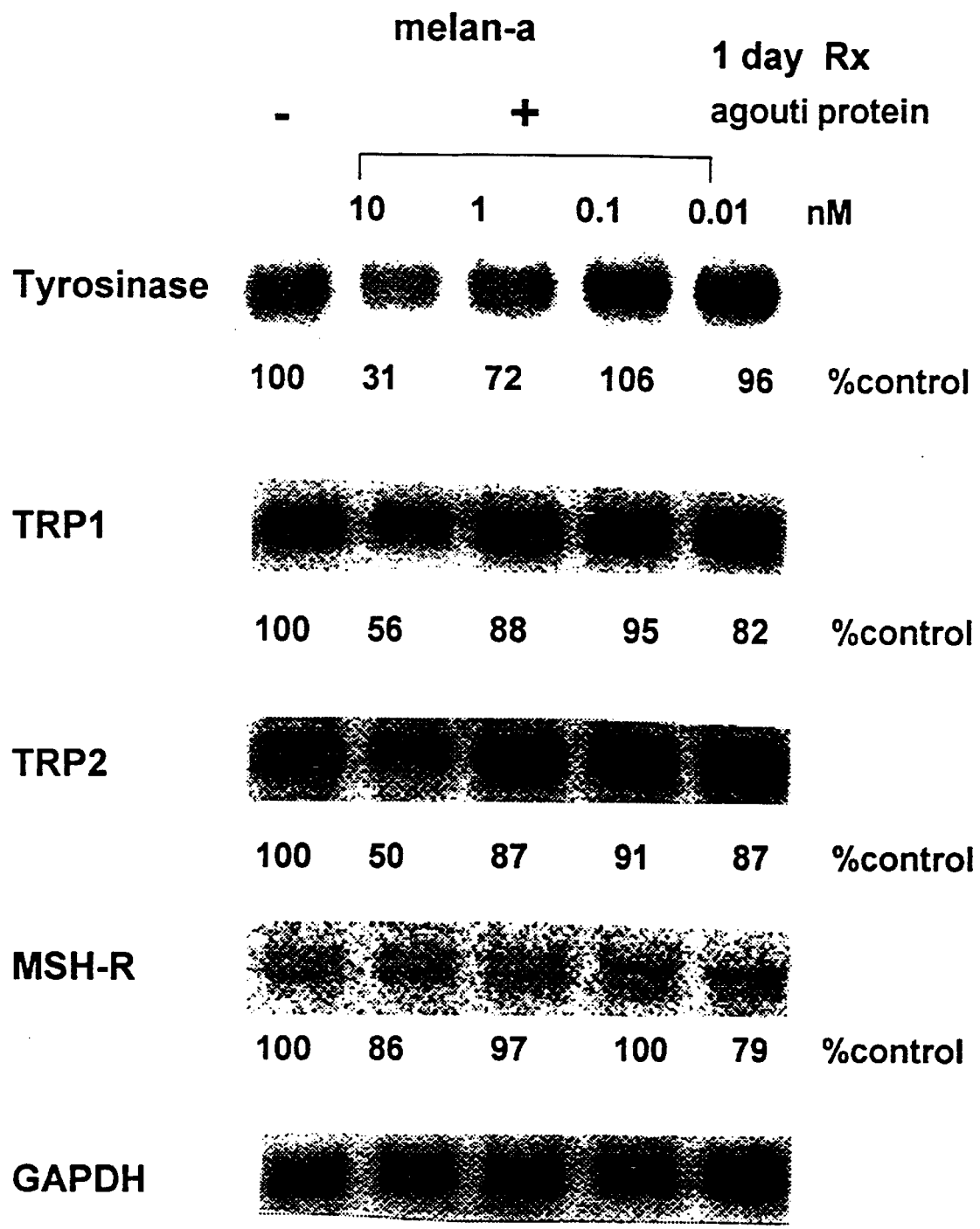
FIG. 9 shows the Northern blot analysis of RNA levels of tyrosinase, TRP 1, TRP 2, MSH-R, and GAPDH from melan-a cells cultured 1 day in the presence of various concentrations of agouti protein or in the absence of agouti protein.

The effects of agouti protein on expression of TRP1, TRP2, and the MSH receptor were examined. After 24 hours of exposure to different concentrations of agouti protein, the level of TRP1 and TRP2 RNAs were reduced, but not to the same extent as tyrosinase RNA, and there was no significant effect on the level of RNA for the MSH receptor (FIG. 9).

Figure 10:
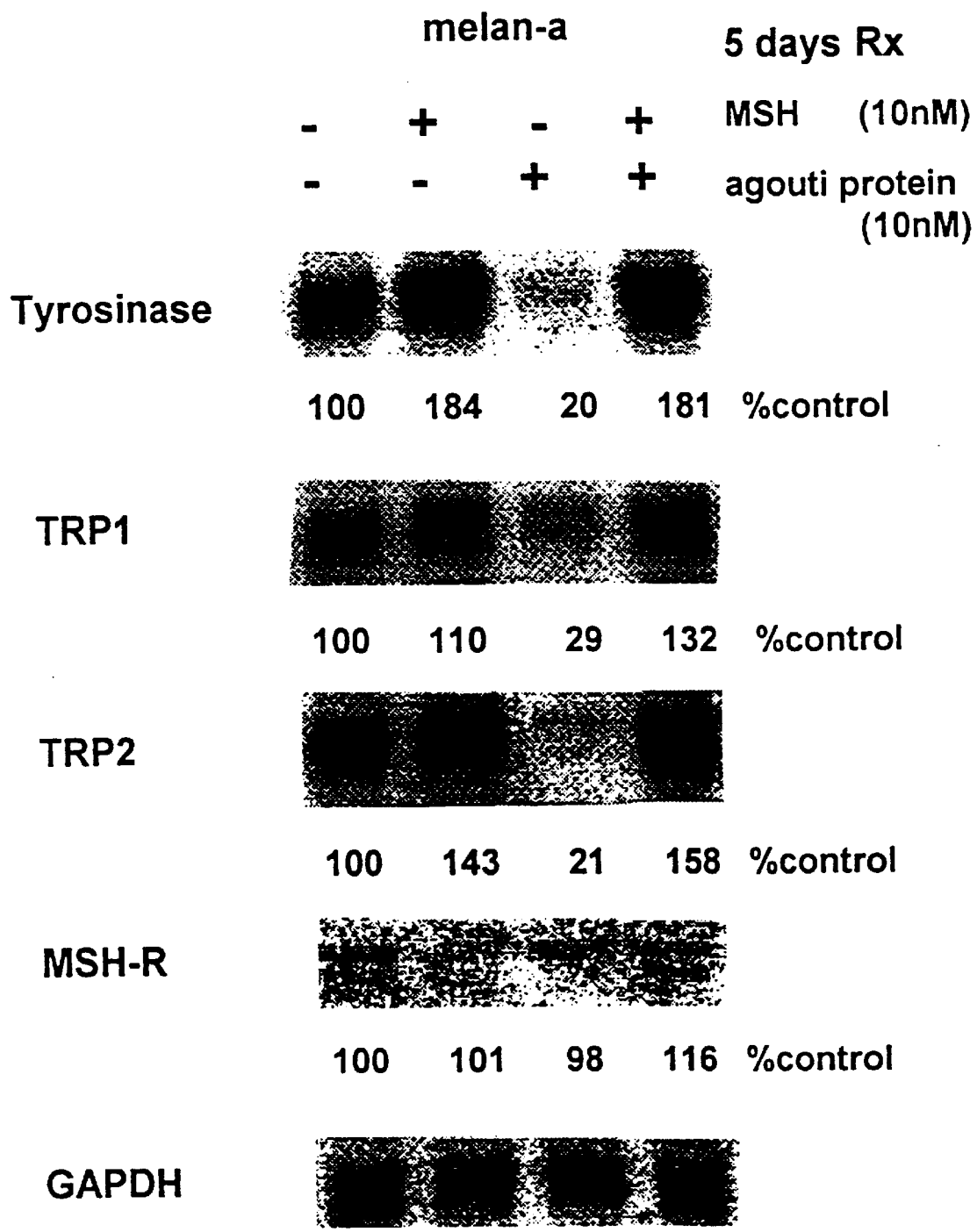
FIG. 10 shows the Northern blot analysis of RNA levels of tyrosinase, TRP 1, TRP 2, MSH-R and GAPDH from melan-a cells cultured 5 days in the presence or absence of 10 nM MSH, in the presence or absence of 10 nM agouti protein, or in the presence of both MSH and agouti protein.

To examine directly the interaction between agouti protein and MSH, and to determine whether agouti protein might affect MSH signaling via a change in receptor level, melan-a cells were exposed to 10 nM agouti, 10 nM MSH, or both for period of 5 days, and then RNA levels were measured for tyrosinase, TRP1, TRP2, and MSH receptor itself. MSH alone produced almost a twofold increase in tyrosinase, a 50% increase in TRP2, and no significant increase in TRP1 or MSH receptor. Agouti alone produced nearly a fivefold decrease in levels of RNA for tyrosinase, TRP1 and TRP2, but again had no significant effect on the level of MSH receptor RNA (FIG. 10). At these concentrations, simultaneous addition of both agouti and MSH produced a response indistinguishable from MSH alone. These results confirm the ability of agouti protein to bring about physiologic changes in the absence of exogenous MSH, and suggest that the interaction of agouti and MSH is not mediated by an alteration in levels of MSH receptor itself.

Figure 11:
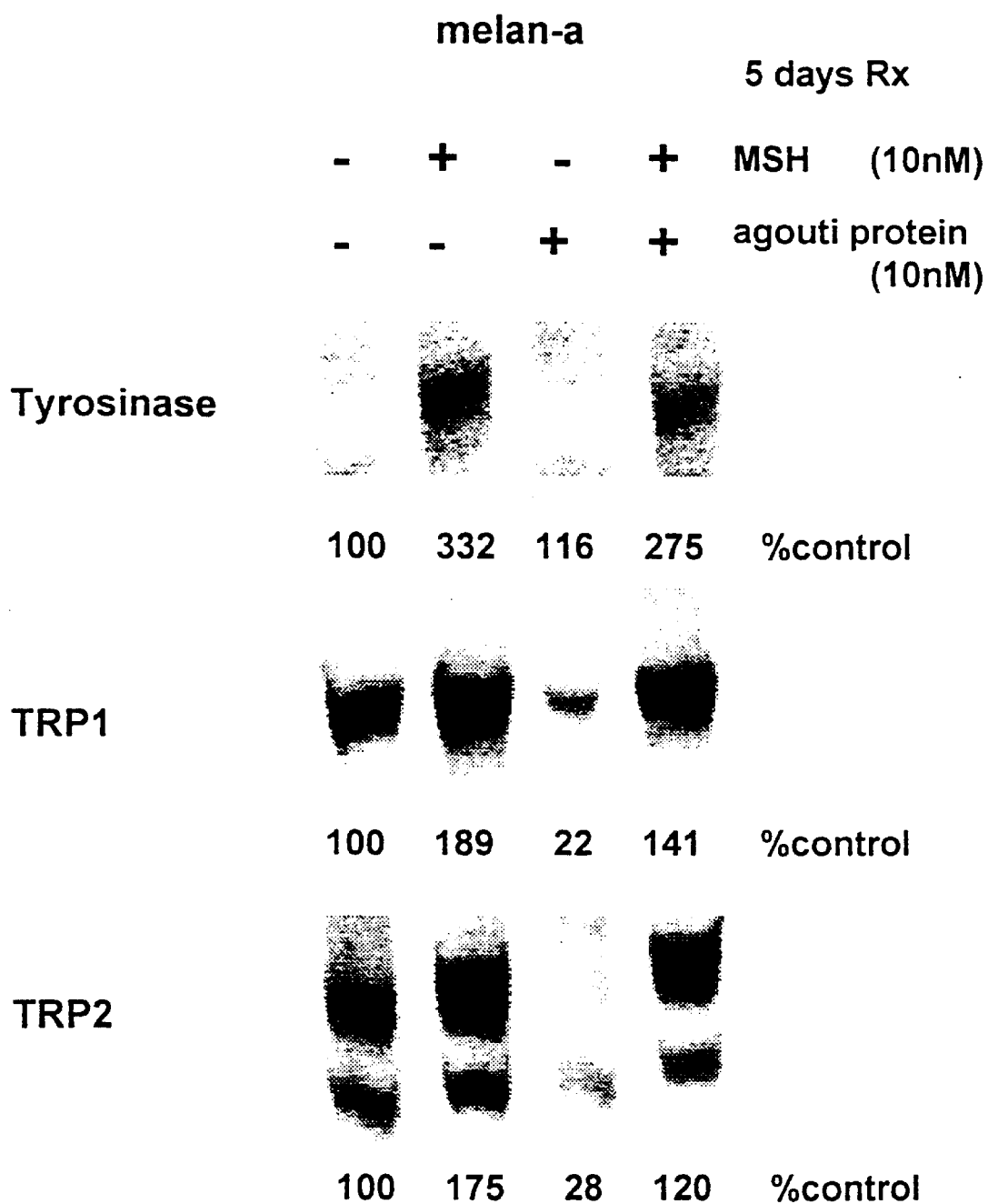
FIG. 11 shows the results of metabolic labeling of immunoprecipitation of tyrosinase, TRP 1 and TRP 2 protein from melan-a cells cultured 5 days in the presence or absence of 10 nM MSH, in the presence or absence of 10 nM agouti protein, or in the presence of both MSH and agouti protein.

However, steady state levels of RNA as measured by Northern hybridization do not reveal alterations in the expression of a gene product that might occur due to modulation of protein levels or protein function. To examine effects at the translational level, the melan-a cells were cultured under the same condition for 5 days, and then the cells were incubated with $^{35}$S methionine for 4 hours. Then, an immunoprecipitation analysis was performed. Results were observed in immunoprecipitation analysis of tyrosinase, TRP1 and TRP2 that were consistent with the Northern blotting (FIG. 11).

To examine enzyme function, enzyme assays was performed on extracts of cells cultured under the same conditions for 5 days. The results of tyrosine hydroxylase, DOPA oxidase, DOPAchrome tautomerase and melanin production assays were also consistent with the Northern blotting experiments. These activities were increased after exposure to MSH alone. However, they were decreased to background levels after exposure to agouti protein alone, and simultaneous addition of both agouti protein and MSH produced a response indistinguishable from MSH alone.

TABLE 3

| | Enzyme Assay* | | | |
|---|---|---|---|---|
| | Control | MSH only | Agouti Only | MSH + Agouti |
| tyrosine hydroxylase | 5.9 ± 1.2 | 8.7 ± 2.8 | −1.2 ± 0.2 | 10.2 ± 1.72 |
| DOPA oxidase | 17.3 ± 5.1 | 197.5 ± 17.4 | −2.6 ± 3.4 | 202.4 ± 24.0 |
| DOPA chome tautomerase | 255.0 | 555.0 | 0.0 | 450.0 |
| melanin production | 2.1 ± 0.6 | 6.3 ± 0.5 | 0.22 ± 0.0 | 6.99 ± 0.53 |

*measures pmol/μg protein/hr

Figure 12:
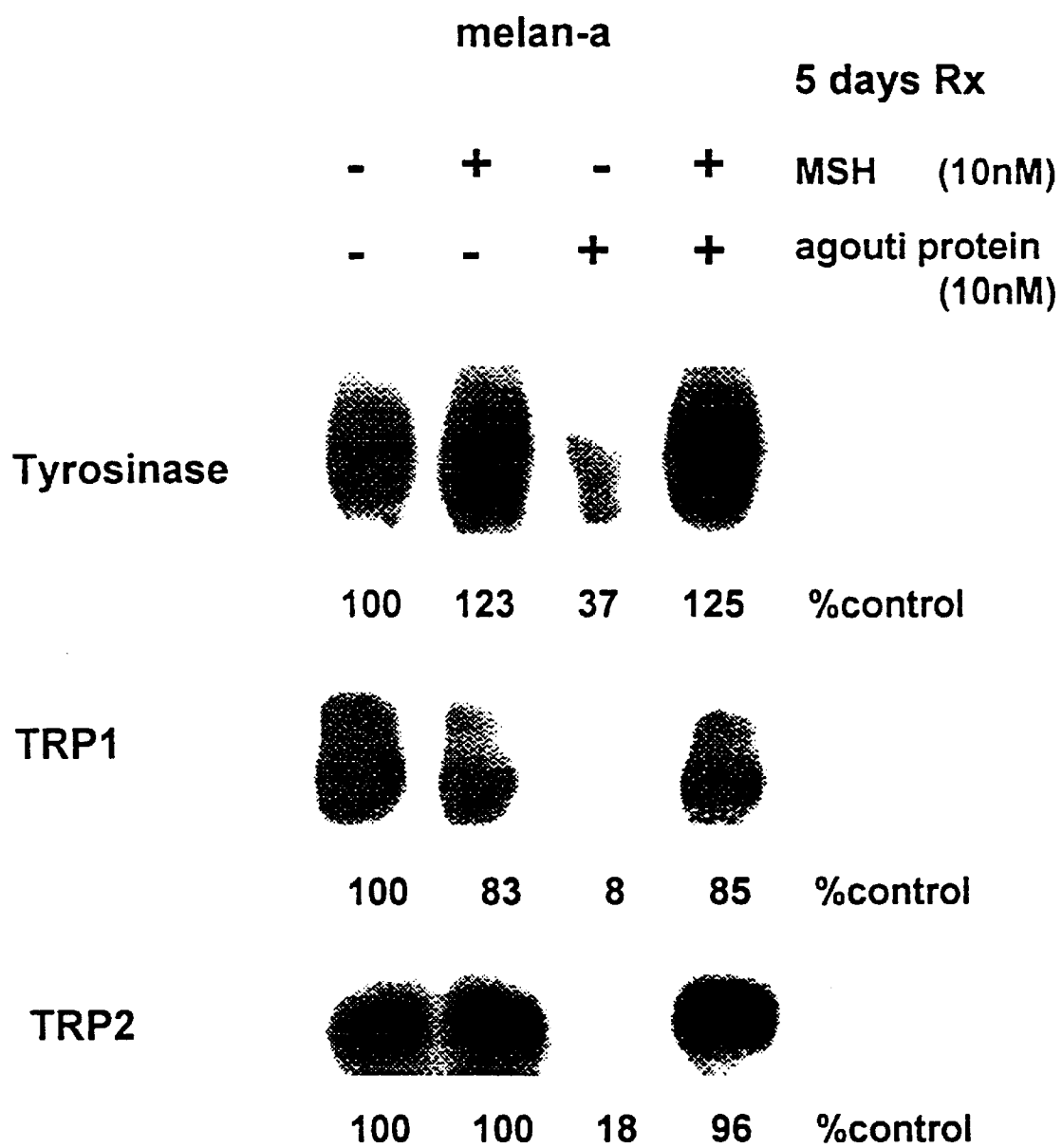
FIG. 12 shows the Western blot of tyrosinase, TRP 1 and TRP 2 protein from melan-a cells cultured 5 days in the presence or absence of 10 nM MSH, in the presence or absence of 10 nM agouti protein, or in the presence of both MSH and agouti protein.

Melanogenic enzyme levels were also examined using Western blotting under the same conditions, and the results also were again consistent with Northern blotting (FIG. 12). These results suggest that modulation of pigment cell enzyme activity by agouti protein or MSH in culture occurs primarily at the level of messenger RNA rather than translational efficiency or post-translational processing.

The effect of agouti protein and MSH observed for melan-a cells was confirmed using B16F10 murine melanoma cells. Similar effects were observed (FIG. 13). However, note that the agouti protein did not reduce tyrosinase RNA below baseline, and that MSH receptor expression was elevated in these agouti-treated cells.

Agouti protein added to melan-a cells suppresses the expression of tyrosinase, TPR1 and TRP2, and causes phenomelanosomes to be produced in vitro. This assay system is useful for helping to determine the molecular and biochemical events required for pigment type switching.

EXAMPLE 6

Human Skin Equivalent Model

The behavior of human melanocytes in the skin equivalent model closely mimics their behavior in vivo. Therefore, the results obtained using the model are reasonably predictive of efficacy in humans. The skin equivalent model has been described by Archambault, M. et al, *J. Invest. Dermatol.* 104(5):859–867, 1995.

Briefly, human newborn fibroblasts are cultivated from explants of foreskin dermis in Dulbecco's modified Eagle's medium (Gibco/BRL, Gaithersburg, Md.) supplemented with 10% bovine serum (Hyclone Labs, Logan, Utah) and used at sixth passage.

Human melanocytes are cultured from dissociated newborn foreskin epidermis. Melanocytes at second passage are plated on a dermal equivalent or in tissue culture in tissue culture dishes (Becton-Dickinson, Lincoln Park, N.J.).

Human keratinocyte cultures are established from newborn foreskin. Preconfluent second-passage keratinocyte cultures are trypsinized and seeded onto dermal equivalents.

Agouti signaling protein or peptides thereof are added to the cultures and the cells incubated for 1 to 5 days. The inhibitory effect on the human melanocytes is determined by Northern blot analysis, Western blot analysis and enzymes assays of tyrosinase, TRP1, TRP2 as described previously in Examples 1 and 5.

EXAMPLE 7

Modulation of Expression and Activity of Melanosomal Proteins in Murine Melanocytes by Agouti Signal Protein in Cell Culture Cells and Cell Culture Conditions The melan-a melanocyte line (Bennett et al., 1987), derived from C57B1 nonagouti black mice (a/a B/B C/C), was a kind gift from Dr. Dorothy Bennett, London, United Kingdom. This clonal line was cultured in Dulbecco's minimal essential medium containing penicillin, streptomycin, sodium pyruvate, nonessential amino acids, 25 mM sodium bicarbonate, 5% fetal bovine serum, 200 nM phorbol-12-myristate-13-acetate and 100 $\mu$M 2-mercaptoethanol at pH 6.9, as described by Bennett et al. (1987). Cells were usually seeded at a density of $1.5 \times 10^6$ cells per 15 cm diameter dish. For 24 hour experiments, ASP and/or MSH were added when the cells were initially seeded. For 5 day experiments, ASP was added immediately, and MSH was added staring on the next day (4 days of treatment with MSH is routinely used for optimal stimulation (Aroca et al., 1993)). The concentrations of ASP and MSH used ranged from 0.01 to 10 nM, as detailed in the Figure and Table legends. To controls without ASP or MSH, similar volumes of storage buffer (20 mM PIPES, pH 6.8, 50 mM NaCl) were added. The cells were routinely cultured at 37° C. in a humidified incubator with 5% $CO_2$, and all media were changed daily. Cells were harvested by brief treatment with trypsin/EDTA in the standard manner, and used for subculture, or were processed for RNA, protein or enzyme analysis, as detailed below.

Agouti Signal Protein

Recombinant mouse ASP was generated and purified using a baculovirus expression system as described in Ollmann et al. (in preparation). The preparation used for most of the experiments described here is $\geq 90\%$ pure as estimated by analysis of silver-stained gels and inhibits activation of the MC1-R with a $K_i$ of $2.2 \times 10^{-10}$ M. At 37°, ASP retains activity for more than 48 hours in water or tissue culture media. The experiment described in FIG. 2 has also been repeated with an ASP preparation $\geq 99\%$ pure with virtually identical results.

Electron Microscopy

Cells were harvested, centrifuged for 5 minutes at 14,000 g at 4° C., and fixed for 2 hours at 23° C. in 2% glutaraldehyde-2% paraformaldehyde in 0.1 M sodium cacodylate buffer, pH 7.3; the fixative was then removed and the samples were stored in phosphate-buffered saline containing 2% sucrose at 4° C. Samples were subsequently processed with graded alcohols and embedded in epoxy resin for electron microscopy in the usual manner. Thin sections were stained with uranyl acetate and lead citrate, viewed and photographed with a Zeiss EM10 electron microscope, as previously detailed (Prota et al., 1995).

RNA Isolation and Northern Blotting

Total RNA was extracted from cells using an RNeasy total RNA isolation kit (QIAGEN, Catsworth, Calif.), following the manufacturer's instructions. 20 $\mu$g of total RNA was denatured, electrophoresed through 1.0% agarose gels, and transferred overnight at 23° C. to SureBlot nylon hybridization membranes (Oncor, Gaithersburg, Md.) in the standard manner. Filters were prehybridized for 3 hours at 45° C. with Hybrisol I solution (Oncor, 50% formamide, 10% dextran sulfate, 1% SDS and blocking reagent), and then hybridized with a $^{32}$P-labeled probe. A 2.0-kb EcoRI fragment of TYRS-J, a 1.7-kb HindIII fragment of pMT4, a 1.75-kb EcoRI fragment of TRP2a, and a 2.1-kb BamHI-SalI fragment of A26 were used to detect tyrosinase, TRP1, TRP2 and MC1-R mRNAs, respectively. TYRS-J was obtained from Drs. Hiroaki Yamamoto and Takuji Takeuchi, Sendai Japan (Yamamoto et al., 1987); pMT4 was obtained from Dr. Shigeki Shibahara, Sendai, Japan (Shibahara et al., 1986); TRP2a was obtained from Dr. Ian Jackson, Edinburgh, Scotland (Jackson et al., 1992); A26 was obtained from Dr. Roger Cone, Oregon (Mountjoy et al., 1992). A commercially available cDNA probe specific for glyceraldehyde-3-phospho-dehydrogenase (GAPDH) was used to standardize RNA loading on the blots. The cDNA probes were labeled using random primer extension and heated to 100° C. for 10 minutes, then cooled on ice for 10 minutes prior to adding to the hybridization solution. Hybridization was performed with the radiolabeled probes in Hybrisol I ($3 \times 10^7$ cpm/10 ml) overnight at 45° C. with gentle shaking. Following the incubation, the blots were washed for 10 minutes at 23° C. with 2×SSC/10% SDS, then for 10 minutes with 0.2×SSC/0.5% SDS, and finally for 10 minutes with 0.1×SSC/0.1% SDS. The blots were then exposed in phosphoroimager cassettes at 23° C. for 1 hour and the densities of the bands were scanned using ImageQuant software. The % control for each probe was corrected for initial loading using comparison with the GAPDH standard. After each scan, residual probe was removed by incubating for 15 minutes at 100° C. in 0.1× SSC/0.1% SDS in 10 mM Tris, pH7.0. This was repeated as necessary until no remaining probe could be detected.

Metabolic Labeling and Immunoprecipitation

These techniques were performed as previously reported (Jiménenez et al., 1989; 1991; Tsukamoto et al., 1992; Aroca et al., 1993). Briefly, subconfluent cells growing in culture in 10 cm diameter dishes were preincubated for 1 hour at 37° C. in prewarmed methionine-free medium, and then were radiolabeled for 6 hours with 0.4 mCi/flask of [$^{35}$S] methionine. The cells were then harvested and solubilized for 1 hour at 4° C. with NP-40/SDS buffer (1% Nonidet P-40, 0.01% SDS, 0.1M Tris-HCl, pH 7.2, 100 $\mu$M phenylmethylsulfonylfluoride, 1 $\mu$g/ml aprotinin). The cell lysates were then centrifuged for 15 minutes at 14,000 g at 4° C., and the supernatants were pretreated overnight at 4° C. with normal rabbit serum and GammaBind G Sepharose (Pharmacia/LKB, Piscataway, N.J.) to reduce background. 5×10$^6$ cpm of each preabsorbed supernatant was then incubated with 10 $\mu$l of the appropriate antibodies. The antibodies used were generated in rabbits against synthetic peptides corresponding to the unique carboxyl sequences of the three melanogenic proteins studied; they are termed $\alpha$PEP1 (which recognizes TRP1, (Jiménez et al., 1991)), $\alpha$PEP7 (which recognizes tyrosinase, (Jiménez et al., 1991)) and $\alpha$PEP8 (which recognizes TRP2, (Tsukamoto et al., 1992)). Following incubation at 37° C. for 1 hour, 50 $\mu$l of GammaBind G Sepharose was added to each tube and then further incubated with mixing for 20 minutes at 23° C. The GammaBind G Sepharose-antigen-antibody immune complexes were washed 4 times with NP40/SDS buffer at 23° C., and then denatured in SDS sample buffer by heating to 100° C. for 3 minutes. Specifically bound proteins were then analyzed by SDS-polyacrylamide gel electrophoresis and visualized by autoradiography.

Western Immunoblotting Analysis

Cells in tissue culture were harvested and solubilized for 1 hour at 4° C. with NP-40/SDS buffer, then centrifuged at 14,000 g for 15 minutes at 4° C., and the supernatants were recovered. Proteins from the NP-40/SDS solubilized cells were separated on 7.5% SDS gels, and then transferred electrophoretically to polyvinylidene difluoride membranes (Immobilon-P, Milipore Corp., Bedford, Mass.). Following blocking overnight at 23° C. in 3% bovine serum albumin in TBS/Tween (0.1% Tween 20 in Tris buffered saline), the blots were incubated with primary antibodies (at 1/1000 dilution in TBS/Tween). Following four washes in TBS/Tween to reduce nonspecific binding, subsequent visualization of specific antibodies bound was carried out with Enhanced ChemiLuminescence (Amersham Corp., Arlington Heights, Ill.) according to the manufacturer's instructions.

Melanogenic Enzyme Assays

Melanogenic assays were routinely carried out on NP40/SDS soluble extracts (obtained as above) at pH 6.8, 37° C. for 60 minutes. To determine tyrosinase activity, the tyrosine hydroxylase assay was used; this assay measures tritiated water produced during the hydroxylation of L-[3,5-$^3$H] tyrosine to 3,4-dihydroxyphenylalanine (DOPA) (Hearing and Ekel, 1976; Hearing, 1987). For DOPA oxidase activity, the production of acid insoluble melanin product from [3-$^{14}$C]DOPA was measured (Aroca et al., 1993). To determine DOPAchome tautomerase activity, the disappearance of DOPAchome substrate and the production of 5,6dihydroxyindole-2-carboxylic acid (DHICA) rather than the spontaneously derived product 5,6-dihydroxyindole (DHI) was measured by HPLC (Palumbo et al., 1987; Tsukamoto et al., 1992). To determine melanin production, the [U-$^{14}$C]tyrosine assay (Hearing and Ekel, 1976; Hearing, 1987) was used. All radioactive precursors were obtained from DuPont-New England Nuclear. DOPAchrome was prepared using the silver oxide method (Körner and Pawelek, 1980), and DHI and DHICA used as standards were obtained from Pierce Chemical Co. (Rockford, Ill.) and from Prof. Shosuke Ito, Nagoya, Japan. Pmol product of the assays was calculated from radioactivity measured or by comparison with standard curves.

cAMP Assays

These assays were performed as previously detailed (Barker et al., 1995; Medrano et al., 1995). Briefly, cells were plated into 24 well plates at a density of 3×10$^5$ cells per well and allowed to grow with a single change of medium for 48 hours. The media were then removed from each well, and the cells were incubated for 40 minutes in the presence of $\alpha$MSH, ASP and/or cholera toxin, following which the reactions were stopped with 1 N HCl. Each sample was then acetylated by the addition of trieethylamine and acetic anhydride and the amount of cAMP was determined by radioimmunoassay as previously detailed (Liggett et al., 1989).

Chemical Analysis

Chemical degradation and analysis of eumelanin and pheomelanin contents were performed and quantitated as previously reported (Ito and Fujita, 1985).

Molecular and biochemical mechanisms that switch melanocytes between the production of eumelanin or pheomelanin involve the opposing action of two intercelluar signalling molecules, $\alpha$-melanocyte stimulating hormone and agouti signal protein. In this study, the physiological effects of agouti signal protein on melanosomal protein expression by eumelanogenic melanocytes in culture treated with purified recombinant agout signal protein were characterized. Following exposure of black melan-a murine melanocytes to agouti signal protein in vitro, pigmentation of the cells was markedly inhibited and the production of eumelanosomes was decreased significantly. In addition, the melanosomes that were produced became pheomelanosome-like in structure and chemical analysis showed that while eumelanin production was significantly decreased, the synthesis of pheomelanin was increased. Melanocytes treated with agout signal protein alone also exhibited time- and dose- dependent decreases in mRNA and protein content of several melanosomal proteins, including the melanogenic enzymes tyrosinase and tyrosinase-related proteins 1 and 2. Conversely, melanocytes exposed to $\alpha$-melanocyte stimulating hormone alone exhibited an increase in tyrosinase mRNA and protein. Simultaneous addition of agouti signal protein and $\alpha$-melanocyte stimulating hormone at approximately equimolar concentrations produced responses similar to those elicited by $\alpha$-melanocyte stimulating hormone alone. These data are consistent with the hypothesis that the effects of agouti signal protein on melanocytes are not mediated solely by inhibition of $\alpha$-melanocyte stimulating hormone binding to its receptor, and provide a cell culture model to identify novel factors whose presence is required for pheomelanogenesis.

REFERENCES

1. Aroca, P., et al., (1990), Biochim. Biophys. Acta, 1035:266–275.
2. Aroca, P., et al., (1993), J. Biol. Chem., 268:25650–25655.
3. Barber, J. I., et al., (1984), J. Invest Dermatol., 83:145–149.
4. Barber, J. I., et al., (1985), J Hered., 76:59–60.
5. Bennett, D. C., et al., (1987), Int. J. Cancer, 39:414–418.
6. Bultman, S. J., et al., (1992), Cell, 71:1195–1204.
7. Burchill, S. A., et al., (1986), J. Endocrinol., 109:15–21.
8. Burchill, S. A., et al., (1989), J. Invest Dermatol., 93:236–240.
9. Chiu, E., et al., (1993), Exp. Eye Res., 57:301–305.
10. Conklin, B. R., et al., (1993), Nature, 364:110.
11. Del-Marmol, V., et al., (1993), FEBS Lett., 327:307–310.
12. Duhl, D. M. J., et al., (1994a), Nature Genet., 8:59–65.
13. Duhl, D. M. J., et al., (1994b), Development, 120:1695–1708.
14. Granholm, N. H., et al., (1990), Pigment Cell Res., 3:233–242.
15. Halaban, R., et al., (1988), Proc. Nat Acad Sci., U.S.A., 85:7241–7245.
16. Hearing, V. J., et al., (1976), Biochem. J., 157:549–557.
17. Hearing, V. J., (1987), Meth. Enzymol., 142:154–165.
18. Hearing, V. J., et al., (1993), FASEB J., 5:2902–2909.
19. Hearing, V. J., and King, R. A., et al., (1993). Determinants of skin color: melanocytes and melanization. In Pigmentation and Pigmentary Abnormalities (ed. N. Levine), pp. 3–32. CRC Press, New York.
20. Hirobe, T., (1982), J. Exp. Zool., 224:355–363.
21. Hirobe, T., (1991), Pigment Cell Res., 5:1–11.
22. Imokawa, G., et al., (1988), J. Invest. Dermatol., 91:106–113.
23. Ito, S., (1993a). Biochemistry and physiology of melanin. In Pigmentation and Pigmentary Disorders (ed. N. Levine), pp. 33–59. CRC Press, Boca Raton.
24. Ito, S., (1993b), J. Invest. Dermatol., 100:166S–171S.
25. Ito, S., et al., (1985), Anal. Biochem., 144:527–536.
26. Jackson, I. J., et al., (1992), EMBO J., 11:527–535.
27. Jimenez, M., et al., (1989), J. Biol. Chem., 264:3397–3403.
28. Jimenez, M., et al., (1991), J. Biol. Chem., 266:1147–1156.
29. Jimenez-Cervantes, C., et al., (1994), J. Biol. Chem., 269:17993–18001.
30. Kappenmann, K. E., et al., (1992), Pigment Cell Res., 5:79–83.
31. Kobayashi, T., et al., (1994a), J. Biol. Chem., 269:29198–29205.
32. Kobayashi, T., et al., (1994b), EMBO J., 13:5818–5825.
33. Kobayashi, T., et al., (1994c), Pigment Cell Res., 7:227–234.
34. Korner, A. M., et al., (1980), J. Invest. Dermatol., 75:192–195.
35. Komer, A. M., et al., (1982), Science, 217:1163–1165.
36. Kwon, B. S., et al., (1991), Proc. Nat Acad. Sci., U.S.A., 88:9228–9232.
37. Laemmli, U. K., (1970), Nature, 227:680–685.
38. Lamoreux, M. L., (1986), Genetics, 113:967–984.
39. Lamoreux, M. L., et al., (1994), Pigment Cell Res., 7:28.
40. Lu, D., et al., (1994), Nature, 371:799–802.
41. Miller, M. W., et al., (1993), Genes Dev., 7:454–467.
42. Movaghar, M., et al., (1987), J Exp. Zool., 243:473–480.
43. Moyer, F. H., (1963), Ann. NY Acad. Sci., 100:584–606.
44. Orlow, S. J., et al., (1994), J. Invest. Dermatol., 103:196–201.
45. Palumbo, A, et al., (1987), Biochim. Biophys. Acta, 925:203–209.
46. Prota, G., (1992), Melanins and Melanogenesis. Academic Press, New York, N.Y. pp. 1–290.
47. Prota, G., et al., (1995), Pigment Cell Res. (in press).
48. Rosemblat, S., et al., (1994), Proc. Nat. Acad. Sci. U.S.A., 91:12071–12075.
49. Sakurai, T., et al., (1975), Dev. Biol., 47:466–471.
50. Silvers, W. K., (1958), J. Exp. Zool., 137:189–196.
51. Silvers, W. K., (1979), The Coat Colors of Mice: A Model for Mammalian Gene Action and Interaction. pp. 1–380. Springer-Verlag, Basel.
52. Tamate, H. B., et al., (1989), J. Exp. Zool, 250:304–311.
53. Thody, A. J., et al., (1992), Pigment Cell Res., 5:335–339.
54. Tripathi, R. K., et al., (1992), J. Biol. Chem., 267:23707–23712.
55. Tsukamoto, K., et al., (1992), EMBO J., 11:519–526.
56. Winder, A. J., et al., (1993), J. Cell Sci., 104:467–475.
57. Winder, A. J., et al., (1994), Cell. Mol. Biol. Res., 40:613–626.
58. Zhou, B. K., et al., (1994), Proc. Nat. Acad. Sci. U.S.A., 91:7076–7080.
59. Yamamoto et al. (1987) Jpn. J. Gen. 62, 271–274,
60. Shibahara et al. (1986) Nucl. Acids Res. 14, 2413–2427
61. Mountjoy et al. (1992) Science 257, 1248–1251.

What is claimed is:

1. A purified biologically active peptide of the human agouti signaling protein with the following characteristics:
   (a) the peptide has depigmenting activity due to its ability to inhibit the production of at least one melanin;
   (b) the peptide comprises a region selected from the group consisting of:
      (i) a basic region derived from the full length agouti signaling protein or a portion of the basic region derived from a full length agouti signaling protein; and
      (ii) a cysteine rich region derived from the full length agouti signaling protein or a portion of the cysteine rich region derived from the full length agouti signaling protein,
   (c) the selected region comprises a minimum length of 9 amino acid residues but comprises a maximum length selected from the group consisting of:
      (i) about 109 amino acid residues;
      (ii) about 50 amino acid residues;
      (iii) about 20 amino acid residues; and
      (iv) about 10 amino acid residues.

2. The peptide of claim 1, comprising the sequence of SEQ ID NO:4.

3. The peptide of claim 1, comprising the sequence of SEQ ID NO:6.

4. The peptide of claim 1, comprising the sequence of SEQ ID NO:8.

5. The peptide of claim 1, comprising the sequence of SEQ ID NO:10.

6. The peptide of claim 1, comprising the sequence of SEQ ID NO:12.

7. The peptide of claim 1, comprising the sequence of SEQ ID NO:14.

8. The peptide of claim 1, comprising the sequence of SEQ ID NO:16.

9. The peptide of claim 1, comprising the sequence of SEQ ID NO:18.

10. The peptide of claim 1, comprising the sequence of SEQ ID NO:20.

11. The peptide of claim 1, comprising the sequence of SEQ ID NO:22.

12. The peptide of claim 1, comprising the sequence of SEQ ID NO:23.

13. A purified biologically active peptide with the following characteristics:
   (a) the peptide has depigmenting activity due to its ability to inhibit the production of at least one melanin;
   (b) the peptide comprises the sequence of SEQ ID NO:24;
   (c) the peptide comprises a maximum length selected from the group consisting of:
      (i) about 109 amino acid residues;
      (ii) about 50 amino acid residues;
      (iii) about 20 amino acid residues; and
      (iv) about 10 amino acid residues.

14. The peptide of claim 1, comprising the sequence of SEQ ID NO:26.

15. The peptide of claim 1, comprising the sequence of SEQ ID NO:28.

16. A composition comprising the peptide of claim 1 and a pharmaceutically acceptable carrier.

17. A method of down-regulating, in a subject with a hyperpigmentary condition, a melanogenic enzyme involved in melanin synthesis, comprising administering to the subject an amount of the peptide of claim 1 effective to down-regulate the melanogenic enzyme and to reduce melanin overproduction.

18. A method of reducing melanin synthesis in a subject with a hyperpigmentary condition, comprising administering to the subject an amount of the peptide of claim 1 effective to reduce melanin synthesis enzyme and to reduce melanin overproduction.

19. A method of reducing melanin synthesis in a subject with a hyperpigmentary condition, comprising administering to the subject an effective amount of a nucleic acid that hybridizes to a nucleic acid encoding the peptide of claim 1, whereby an agouti signaling protein-encoding nucleic acid is not transcribed, melanin synthesis is reduced, and melanin overproduction is reduced.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
      (A) LENGTH: 131 amino acids
      (B) TYPE: amino acid
      (C) STRANDEDNESS: not relevant
      (D) TOPOLOGY: linear (ii) MOLECULE TYPE: peptide (xi) SEQUENCE DESCRIPTION: SEQ ID NO: 1:

```
Met Asp Val Thr Arg Leu Leu Leu Ala Thr Leu Val Ser Phe Leu Cys
1               5                   10                  15

Phe Phe Thr Val His Ser His Leu Ala Leu Glu Glu Thr Leu Gly Asp
                20                  25                  30

Asp Arg Ser Leu Arg Ser Asp Ser Ser Met Asn Ser Leu Asp Phe Ser
```

```
              35                  40                  45
Ser Val Ser Ile Val Ala Leu Asn Lys Lys Ser Lys Lys Ile Ser Arg
         50                  55                  60

Lys Glu Ala Glu Lys Arg Lys Arg Ser Ser Lys Lys Lys Ala Ser Met
 65                  70                  75                  80

Lys Lys Val Ala Arg Pro Pro Pro Ser Pro Cys Val Ala Thr Arg
                 85                  90                  95

Asp Ser Cys Lys Pro Pro Ala Pro Ala Cys Cys Asp Pro Cys Ala Ser
                100                 105                 110

Cys Gln Cys Arg Phe Phe Gly Ser Ala Cys Thr Cys Arg Val Leu Asn
                115                 120                 125

Pro Asn Cys
        130
```

(2) INFORMATION FOR SEQ ID NO: 2:

(i) SEQUENCE CHARACTERISTICS:
        (A) LENGTH: 130 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 2:

```
Met Asp Val Thr Arg Leu Leu Leu Ala Thr Leu Leu Gly Phe Leu Cys
 1               5                  10                  15

Phe Phe Thr Ala Asn Ser His Leu Pro Pro Glu Glu Lys Leu Arg Asp
                 20                  25                  30

Asp Arg Ser Leu Arg Ser Asp Ser Ser Val Asn Leu Leu Asp Val Pro
                 35                  40                  45

Ser Val Ser Ile Val Ala Leu Asn Lys Lys Ser Lys Gln Ile Gly Arg
         50                  55                  60

Lys Ala Ala Glu Lys Lys Arg Ser Ser Lys Lys Glu Ala Ser Met
 65                  70                  75

Lys Lys Val Val Arg Pro Pro Pro Ser Pro Cys Val Ala Thr Asn
 80                  85                  90                  95

Asp Ser Cys Lys Pro Pro Ala Pro Ala Cys Cys Asp Pro Cys Ala Ser
                100                 105                 110

Cys Gln Cys Arg Phe Phe Gly Arg Ala Cys Ser Cys Arg Val Leu Ser
                115                 120                 125

Leu Asn Cys
        130
```

(2) INFORMATION FOR SEQ ID NO: 3:

(i) SEQUENCE CHARACTERISTICS:
        (A) LENGTH: 64 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 3:

```
His Leu Ala Leu Glu Glu Thr Leu Gly Asp Asp Arg Ser Leu Arg Ser
 1               5                  10                  15

Asp Ser Ser Met Asn Ser Leu Asp Phe Ser Ser Val Ser Ile Val Ala
                 20                  25                  30
```

```
Leu Asn Lys Lys Ser Lys Lys Ile Ser Arg Lys Glu Ala Glu Lys Arg
        35                  40                  45

Lys Arg Ser Ser Lys Lys Ala Ser Met Lys Lys Val Ala Arg Pro
    50                  55                  60

(2) INFORMATION FOR SEQ ID NO: 4:

(i) SEQUENCE CHARACTERISTICS:
        (A) LENGTH: 63 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 4:

His Leu Pro Pro Glu Glu Lys Leu Arg Asp Asp Arg Ser Leu Arg Ser
1               5                   10                  15

Asp Ser Ser Val Asn Leu Leu Asp Val Pro Ser Val Ser Ile Val Ala
            20                  25                  30

Leu Asn Lys Lys Ser Lys Gln Ile Gly Arg Lys Ala Ala Glu Lys Lys
        35                  40                  45

Arg Ser Ser Lys Lys Glu Ala Ser Met Lys Lys Val Val Arg Pro
    50                  55                  60

(2) INFORMATION FOR SEQ ID NO: 5:

(i) SEQUENCE CHARACTERISTICS:
        (A) LENGTH: 45 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 5:

Pro Pro Pro Ser Pro Cys Val Ala Thr Arg Asp Ser Cys Lys Pro Pro
1               5                   10                  15

Ala Pro Ala Cys Cys Asp Pro Cys Ala Ser Cys Gln Cys Arg Phe Phe
            20                  25                  30

Gly Ser Ala Cys Thr Cys Arg Val Leu Asn Pro Asn Cys
        35                  40                  45

(2) INFORMATION FOR SEQ ID NO: 6:

(i) SEQUENCE CHARACTERISTICS:
        (A) LENGTH: 45 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 6:

Pro Pro Pro Ser Pro Cys Val Ala Thr Asn Asp Ser Cys Lys Pro Pro
1               5                   10                  15

Ala Pro Ala Cys Cys Asp Pro Cys Ala Ser Cys Gln Cys Arg Phe Phe
            20                  25                  30

Gly Arg Ala Cys Ser Cys Arg Val Leu Ser Leu Asn Cys
        35                  40                  45

(2) INFORMATION FOR SEQ ID NO: 7:

(i) SEQUENCE CHARACTERISTICS:
```

(A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 7:

His Leu Ala Leu Glu Glu Thr Leu Gly Asp
1               5                   10

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 8:

His Leu Pro Pro Glu Glu Lys Leu Arg Asp
1               5                   10

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 9:

Asp Arg Ser Leu Arg Ser Asp Ser Ser Met
1               5                   10

(2) INFORMATION FOR SEQ ID NO: 10:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 10:

Asp Arg Ser Leu Arg Ser Asp Ser Ser Val
1               5                   10

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 11:

Asn Ser Leu Asp Phe Ser Ser Val Ile Val
1               5                   10

(2) INFORMATION FOR SEQ ID NO: 12:

(i) SEQUENCE CHARACTERISTICS:
    (A) LENGTH: 10 amino acids
    (B) TYPE: amino acid
    (C) STRANDEDNESS: not relevant
    (D) TOPOLOGY: linear (ii) MOLECULE TYPE: peptide (xi) SEQUENCE DESCRIPTION: SEQ ID NO: 12:

Asn Leu Leu Asp Val Pro Ser Val Ile Val
 1               5                  10

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 13:

Ala Leu Asn Lys Lys Ser Lys Lys Ile Ser
 1               5                  10

(2) INFORMATION FOR SEQ ID NO: 14:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 14:

Ala Leu Asn Lys Lys Ser Lys Gln Ile Gly
 1               5                  10

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 15:

Arg Lys Glu Ala Glu Lys Arg Lys Arg Ser
 1               5                  10

(2) INFORMATION FOR SEQ ID NO: 16:

(i) SEQUENCE CHARACTERISTICS:
        (A) LENGTH: 9 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 16:

Arg Lys Ala Ala Glu Lys Lys Arg Ser
 1               5

(2) INFORMATION FOR SEQ ID NO: 17:

```
    (i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 17:

Ser Lys Lys Lys Ala Ser Met Lys Lys Val
 1               5                  10

(2) INFORMATION FOR SEQ ID NO: 18:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 18:

Ser Lys Lys Glu Ala Ser Met Lys Lys Val
 1               5                  10

(2) INFORMATION FOR SEQ ID NO: 19:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 19:

Ala Arg Pro Pro Pro Pro Ser Pro Cys Val
 1               5                  10

(2) INFORMATION FOR SEQ ID NO: 20:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 20:

Val Arg Pro Pro Pro Pro Ser Pro Cys Val
 1               5                  10

(2) INFORMATION FOR SEQ ID NO: 21:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 21:

Ala Thr Arg Asp Ser Cys Lys Pro Pro Ala
 1               5                  10
```

```
(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 22:

Ala Thr Asn Asp Ser Cys Lys Pro Pro Ala
1               5                   10

(2) INFORMATION FOR SEQ ID NO: 23:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 23:

Pro Ala Cys Cys Asp Pro Cys Ala Ser Cys
1               5                   10

(2) INFORMATION FOR SEQ ID NO: 24:

(i) SEQUENCE CHARACTERISTICS:
        (A) LENGTH: 15 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 24:

Cys Gly Leu Gly Glu Asn Ser Pro Leu Leu Ser Gly Gln Gln Val
1               5                   10                  15

(2) INFORMATION FOR SEQ ID NO: 25:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 25:

Gln Cys Arg Phe Phe Gly Ser Ala Cys Thr
1               5                   10

(2) INFORMATION FOR SEQ ID NO: 26:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 26:

Gln Cys Arg Phe Phe Gly Arg Ala Cys Ser
1               5                   10
```

-continued (2) INFORMATION FOR SEQ ID NO: 27:

(i) SEQUENCE CHARACTERISTICS:
        (A) LENGTH: 8 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 27:

Cys Arg Val Leu Asn Pro Asn Cys
1            5

(2) INFORMATION FOR SEQ ID NO: 28:

(i) SEQUENCE CHARACTERISTICS:
        (A) LENGTH: 8 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 28:

Cys Arg Val Leu Ser Leu Asn Cys
1            5